(12) United States Patent
Bobbitt et al.

(10) Patent No.: US 10,822,322 B2
(45) Date of Patent: Nov. 3, 2020

(54) MOLECULE WITH ANTI-CANCER ACTIVITY

(71) Applicant: OCEANS LTD., St-Johns (CA)

(72) Inventors: Judith Bobbitt, St-Johns (CA); Ahmed Zein, St-Johns (CA)

(73) Assignee: OCEANS LTD., St. John's (CA)

( * ) Notice: Subject to any disclaimer, the term of this patent is extended or adjusted under 35 U.S.C. 154(b) by 262 days.

(21) Appl. No.: 16/070,864

(22) PCT Filed: Jan. 18, 2017

(86) PCT No.: PCT/CA2017/050053
§ 371 (c)(1),
(2) Date: Jul. 18, 2018

(87) PCT Pub. No.: WO2017/124184
PCT Pub. Date: Jul. 27, 2017

(65) Prior Publication Data
US 2019/0040032 A1 Feb. 7, 2019

Related U.S. Application Data

(60) Provisional application No. 62/280,280, filed on Jan. 19, 2016.

(51) Int. Cl.
*C07D 313/00* (2006.01)
*A61K 36/05* (2006.01)
*A61K 31/365* (2006.01)
*A61K 45/06* (2006.01)
*A61P 35/00* (2006.01)

(52) U.S. Cl.
CPC .......... *C07D 313/00* (2013.01); *A61K 31/365* (2013.01); *A61K 36/05* (2013.01); *A61K 45/06* (2013.01); *A61P 35/00* (2018.01)

(58) Field of Classification Search
CPC ..... C07D 313/00; A61P 35/00; A61K 31/365; A61K 36/05; A61K 45/06
See application file for complete search history.

(56) References Cited

U.S. PATENT DOCUMENTS

2017/0165306 A1* 6/2017 Bobbitt .................. A61P 35/00

FOREIGN PATENT DOCUMENTS

| CA | 2954781 | 1/1917 |
|---|---|---|
| EP | 2484683 | 8/2012 |
| WO | WO 2016/090494 | 6/1916 |
| WO | WO 2016/201559 | 12/1916 |

OTHER PUBLICATIONS

International Search Report issued in International Application No. PCT/CA2017/050053, dated Jul. 27, 2017.

* cited by examiner

*Primary Examiner* — Timothy R Rozof
(74) *Attorney, Agent, or Firm* — Parker Highlander PLLC

(57) ABSTRACT

The present invention provides a new compound of formula (I): extracted from a seaweed, and its use for inhibiting the growth of cancer cells, as well as methods for its extraction and isolation.

14 Claims, 17 Drawing Sheets

MOLECULE WITH ANTI-CANCER ACTIVITY

This application is a national phase application under 35 U.S.C. § 371 of International Application No. PCT/CA2017/050053, filed Jan. 18, 2017, which claims priority to U.S. Provisional Application No. 62/280,280, filed Jan. 19, 2016. The entire text of each of the above referenced disclosures is specifically incorporated herein by reference.

FIELD OF THE INVENTION

The present invention relates to a novel molecule extracted from seaweeds, method of preparation and use for inhibiting the growth of cancer cells.

BACKGROUND OF THE INVENTION

Cancer is a disease that seriously jeopardizes the health of human beings. Around the globe, about 6 million people die of cancer every year, with another 10 millions seriously affected by the disease. According to the estimate of the World Health Organization, in the 21st century, cancer will become the "number one killer" of mankind.

In the several past decades, many ways of treating cancer became available, mainly including surgery, radiotherapy, chemotherapy, hormonotherapy, gene therapy, and immunotherapy, among which surgery, radiotherapy and chemotherapy have become the major means. Chemotherapy refers to treating cancer with chemical medication. It is the most rapidly expanding field in the treatment of cancer. A great number of new medicines aiming at different targets are ready for clinical application, and developments in research in mechanism of drug action and pharmacokinetics have made the clinical administration routes and means more fitting for killing tumor cells while protecting the normal tissues.

The search for natural-derived molecule for inhibiting cancer cells has led to the discovery of molecules such as Taxol or Vinblastine. Despite the utility of *taxus* and *vinca* alkaloids in the clinic, there are serious limitations to these therapies.

One major drawback when treating cancer is to achieve selectivity against this type of cancer cells. There remains a need to discover and isolate new potent compounds having selective activity against certain types of cancer cells, thereby providing highly selective anti-cancer molecules.

Against such a background, new molecules to add to the already existing armada of chemotherapeutic drugs are highly desirable.

SUMMARY OF THE INVENTION

A main aspect intended to be addressed by the present invention is to provide a novel molecule extracted from *Chaetomorpha Cannabina* (CC) seaweed.

According to a first aspect, there is provided an extract enriched in a compound defined by formula (I):

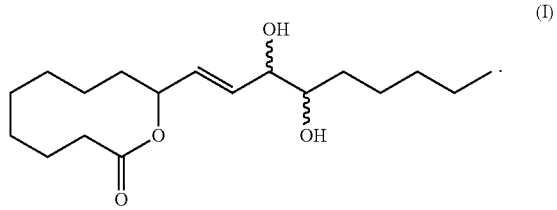 [SMILES: CCCCCC(O)C(O)/C=C/C1CCCCCCCC(=O)O1]

(I)

According to a first aspect, there is provided a compound defined by formula (I) in enriched or purified form.

According to a further aspect of the present invention, there is provided use of the extract or compound as defined herein for inhibiting growth of cancer cells, either in vitro or in vivo, for example in a mammal.

According to a further aspect of the present invention, there is provided use of the extract or compound as defined herein for the manufacture of composition for treating cancer in a mammal.

According to a further aspect, the present invention provides a composition comprising the extract or compound as defined herein, in admixture with a physiologically acceptable excipient.

According to a further aspect, the present invention provides use of the composition as defined herein for the treatment of cancer in a mammal.

According to a further aspect, the present invention provides a method for inhibiting growth of cancer cells comprising contacting said cell with a growth-inhibiting concentration of the extract, the compound, or the composition, as defined herein.

According to a further aspect, the present invention provides a method for treating cancer in a mammal comprising administering a growth-inhibiting concentration of the composition as defined herein to the mammal.

According to a further aspect, the present invention provides a method for isolating a compound as defined herein comprising the steps of:
a) mixing biomass from *Chaetomorpha Cannabina* (CC) seaweed with a first solvent to obtain a biomass:solvent mixture;
b) eluting said mixture in SPE column with various concentrations of a second solvent and recovering a solvent fraction;
c) fractionating said methanol fraction from step b) on Combiflash column with various concentrations of a third solvent, and recovering a fraction containing the compound of formula (I), and optionally, enriching or purifying said compound from said fraction.

DETAILED DESCRIPTION OF THE INVENTION

ABBREVIATIONS AND DEFINITIONS

Figure 1:
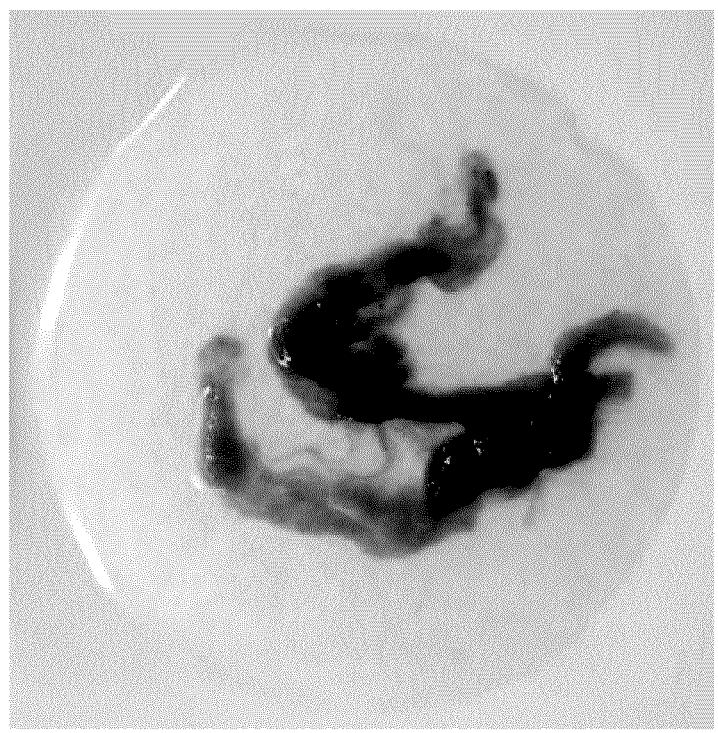
FIG. 1 Picture of a sample of *Chaetomorpha Cannabina* (CC) seaweed used for extraction.

Abbreviations bis-AAF-R110: bis-alanyl-alanyl-phenylalanyl-rhodamine 110; CIMA: colorimetric indicative of metabolic activity; GF-AFC: Gly-Phe-7-amino-4-trifluoromethylcoumarin; HILIC: hydrophilic interaction liquid chromatography. C-18 SPE: solid phase extraction on C-18 column.

Definitions

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The terms "about" or "around" as used herein refers to a margin of + or −10% of the number indicated. For sake of precision, the term about when used in conjunction with, for example: 90% means 90%+/−9% i.e. from 81% to 99%. More precisely, the term about refer to + or −5% of the number indicated, where for example: 90% means 90%+/−4.5% i.e. from 86.5% to 94.5%. When used in the context of a pH, the term "about" means +/−0.5 pH unit.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "subject" or "patient" as used herein refers to an animal, preferably a mammal, and most preferably a human who is the object of treatment, observation or experiment.

"Mammal" includes humans and both domestic animals such as laboratory animals and household pets, (e.g. cats, dogs, swine, cattle, sheep, goats, horses, rabbits), and non-domestic animals such as wildlife and the like.

The term "extract" as used herein means a composition prepared by contacting solvent with seaweed biomass, produced following the procedures of the invention, which demonstrates inhibitory activity against one or more cancer cell line in vitro. In one aspect of the invention, an extract demonstrates inhibitory activity against cancer cell growth in vivo. As used herein, the term "extract" means an extract that is: crude, fractionated, sub-fractionated, separated, isolated, enriched or purified, without being limited thereto.

The term "isolated" is used herein to indicate that the compound exists in a physical milieu distinct from that in which it occurs in nature. For example, the isolated molecule may be substantially isolated (for example enriched or purified) with respect to the complex cellular milieu in which it naturally occurs, such as in a crude extract. When the isolated molecule is enriched or purified, the absolute level of purity is not critical and those skilled in the art can readily determine appropriate levels of purity according to the use to which the biomass is to be put. In some circumstances, the isolated molecule forms part of a composition (for example a more or less crude extract containing many other substances) or buffer system, which may for example contain other components. In other circumstances, the isolated molecule may be purified to essential homogeneity, for example as determined spectrophotometrically, by NMR or by chromatography (for example LC-MS).

The term "crude" means compounds or molecules that have not been entirely separated from the components of the original composition in which it was present. Therefore, the terms "separating", "purifying" or "isolating" refers to methods by which one or more contaminant (i.e. not relevant) components of the biological sample are removed from one or more other desired components of the sample.

The molecule(s) described herein can be formulated as pharmaceutical compositions by formulation with additives such as pharmaceutically acceptable excipients, pharmaceutically acceptable carriers, and pharmaceutically acceptable vehicles, or as nutraceutical or nutritional formulations with additives such as nutraceutically or nutritionally acceptable excipients, nutraceutically or nutritionally acceptable carriers, and nutraceutically or nutritionally acceptable vehicles.

As used herein, the term "pharmaceutically acceptable" refers to molecular entities and compositions that are physiologically tolerable and do not typically produce an allergic or similar unwanted reaction, such as gastric upset, dizziness and the like, when administered to human. Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for injectable solutions. Suitable pharmaceutical carriers are described in "Remington's Pharmaceutical Sciences" by E. W. Martin.

The molecule(s) and composition(s) of the present invention can be prepared as nutritional formulations such as foods, including medical or functional foods and dietary supplements. A "medical or functional food" is defined as being consumed as part of a usual diet but which has been demonstrated to have physiological benefits and/or to reduce the risk of a disease or condition such as a chronic disease, beyond basic nutritional functions. A "dietary supplement" is defined as a product that is intended to supplement the human diet and is typically provided in the form of a pill, capsule, tablet, or like formulation. By way of example, but not limitation, a dietary supplement may include one or more of the following ingredients: vitamins, minerals, herbs, botanicals, amino acids, dietary substances intended to supplement the diet by increasing total dietary intake, and concentrates, metabolites, constituents, extracts or combinations of any of the foregoing. Dietary supplements may also be incorporated into food stuffs, such as functional foods designed to promote health or to prevent disease or disorders. If administered as a medicinal preparation, the composition can be administered, either as a prophylaxis or treatment, to a patient in any of a number of methods. The subject compositions may be administered alone or in combination with other pharmaceutical agents and can be combined with a physiologically acceptable carrier thereof. The effective amount and method of administration and aim of the particular formulation can vary based on the individual subject, the stage of the disease or condition, and other factors evident to one skilled in the art. In the case of a pharmaceutical formulation as well as a nutraceutical formulation, during the course of the treatment, the concentration of the subject compositions may be monitored (for example, blood plasma levels may be monitored) to ensure that the desired level is maintained.

The term "nutraceutical" has been used to refer to any substance that is a food or a part of a food and provides medical or health benefits, including the prevention and treatment of disease or condition. Thus, a nutraceutical is a product isolated or purified from foods that is generally sold in medicinal forms not usually associated with foods. A nutraceutical is demonstrated to have a physiological benefit or provide protection against chronic disease. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease. Suitable nutraceutically-acceptable excipients may include liquid solutions such as a solution comprising a vegetable- and/or animal- and/or fish-derived oil.

The terms "molecule" and "compound" are used herein interchangeably.

DETAILED DESCRIPTION OF PARTICULAR ASPECTS OF THE INVENTION

With the aim of providing an alternative source of anti-cancer molecules, there is provided an anti-cancer compound extracted and isolated from a solvent extract of *Chaetomorpha Cannabina* (CC).

Extract

In accordance with a particular embodiment of the present invention, the bioactive molecule from the above listed seaweeds is found in a 100% MeOH fraction and defined by formula:

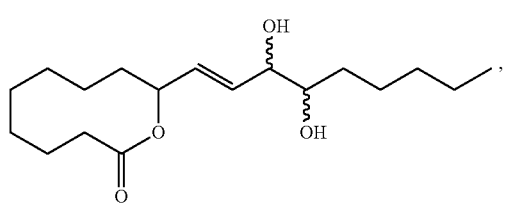

Active Molecule from Extract

According to a particular embodiment, the invention provides a compound as defined by formula (I):

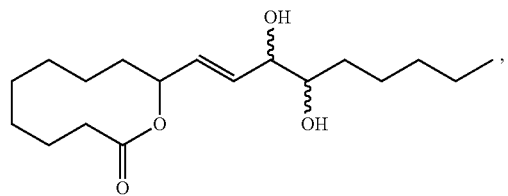

as a racemic mixture or enantiomer thereof.

Composition

In accordance with a particular embodiment of the invention, there is provided a composition comprising the compound as defined herein, in admixture with a physiologically acceptable excipient.

Uses and Methods of Use

In accordance with an alternative embodiment, the present invention provides the use of the compound as defined herein for inhibiting growth of cancer cells. Particularly, there is provided the use of the extract as defined herein for the manufacture of composition for treating cancer in a mammal.

In accordance with an alternative embodiment of the invention, there is provided the use of the composition as defined herein for the treatment of cancer in a mammal.

In accordance with a particular embodiment, the present invention provides a method of inhibiting a cancer cell growth comprising contacting said cell with a growth-inhibiting concentration of the compound as defined herein or the composition as defined herein.

Method of Treatment

More particularly, there is provided a method of treatment of cancer in a mammal comprising administering a growth-inhibiting concentration of the composition as defined herein to said mammal. Most particularly, the mammal is a pet animal or a human.

Method of Extraction and Isolation

In accordance with a particular embodiment, there is provided a method for extracting the compound as defined herein, comprising the steps of:

a) mixing biomass from *Chaetomorpha Cannabina* (CC) seaweed with a first solvent to obtain a biomass:first solvent mixture;

b) eluting said mixture in SPE column with various concentrations of a second solvent and recovering a second solvent fraction;

c) fractionating said methanol fraction from step b) on Combiflash column with various concentrations of a third solvent mixture, and recovering a fraction containing major components.

In accordance with an alternative embodiment, the method of the invention further comprises a hexane-defatting step prior to step a).

In accordance with a particular embodiment, the method further comprises the step of: d) sub-fractionating said fraction on semi-preparative HPLC column with a fourth solvent mixture to obtain a sub-fraction enriched in compound (I).

In accordance with an optional embodiment, the method further comprises the step of: d') enriching or purifying a compound of formula (I) from said sub-fraction:

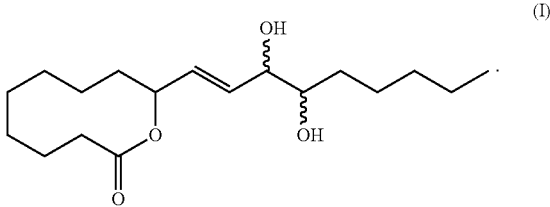 [SMILES: CCCCCC(O)C(O)/C=C/C1CCCCCCCC(=O)O1]

(I)

In accordance with a alternative embodiment, the method further comprises the step of: e) drying said sub-fraction by removing solvent to obtain a dried extract enriched in a compound of formula (I):

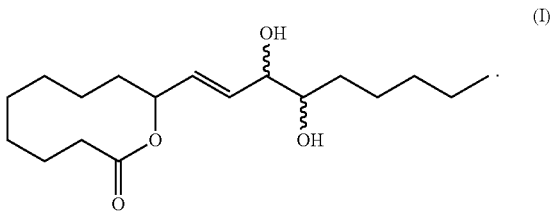 [SMILES: CCCCCC(O)C(O)/C=C/C1CCCCCCCC(=O)O1]

(I)

Solvent for Extraction

Particularly, the molecule is extracted with a first solvent. More particularly, the extract's first solvent is water or alcohol; and even more particularly: aqueous ethanol.

Particularly, the crude extract is an aqueous ethanol extract of CC. More particularly, the crude extract is a: 80%, 75%, 70%, 65%, 60%, 55%, 50%, 45%, 40%, 35%, 30%, 25% aqueous ethanol extract. Even more particularly, the crude extract is an 80% aqueous ethanol extract. Most particularly, the crude extract is a previously hexane-defatted extract.

Particularly, the second solvent is methanol, aqueous methanol or a mixture of methanol and acetonitrile. More particularly, the extract is a C-18 second solvent fraction of the crude extract: particularly a 5%, 10%, 15%, 20%, 25%, 30%, 25%, 40%, 45%, 50%, 55%, 60%, 65%, 70%, 75%, 80%, 85%, 90%, 95% of a second solvent, being particularly: aq. MeOH, or 100% MeOH, or $CH_2Cl_2$:MeOH (1:1). Most particularly, the fraction is from a 30% aqueous MeOH to 100% MeOH fraction.

Particularly, the third solvent is methanol or aqueous methanol. Most particularly, the extract is a flash column sub-fraction of the C-18 fraction. Particularly, the sub-fraction is about 40% MeOH sub-fraction.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES—ANTI-CANCER ACTIVITY OF COMPOUND (I) PURIFIED FROM MARINE SEAWEED HARVESTED FROM NEWFOUNDLAND AND LABRADOR

Example 1—Seaweed Collection and Identification

A collection program for seaweeds was established for different geographical regions of Newfoundland, Labrador and Quebec over several time periods.

The general collection procedure was as follows: seaweeds were collected from the intertidal zone by hand with knives while scuba divers collected seaweed from sub tidal zones. Samples were placed in plastic sampling bags and transported to the laboratory in coolers of seawater. Upon arrival in the laboratory, each species was washed individually to remove epiphytic and extraneous matter (sand, mussels, isopods, etc.). Samples were then checked visually to ensure they were clean. If not, remaining matter was removed by hand with further washing. Seaweeds were blotted dry, weighed to the nearest g (plant wet weight) and shredded. The shredded biomass was transferred into Erlenmeyer flasks and frozen at −60° C. until the extracts were prepared.

A representative sample of different samples of *Chetomorpha cannabina* were also photographed (see FIG. 1) and frozen at −20° C. for confirmation of species by Dr. Robert Hooper, a phycologist at Memorial University of Newfoundland.

Example 2. Extract Preparation 2.1 Freeze-Drying

To prepare samples for extraction the seaweed was first freeze dried. Erlenmeyer flasks containing shredded seaweeds, which had been frozen at −60° C., were placed on a freeze-dryer, and lyophilized for 72-96 h at $69 \times 10^{-3}$ mbar. The weight (g) of dry biomass was then recorded as plant dry weight (g). This step accounts for the differences in water content among seaweeds which may otherwise affect the solubility of bioactive components. Secondary plant metabolites are also more stable when stored in a dried form. Moreover, the large-scale extraction of dried plant biomass may cause fewer problems than extracting fresh biomass. In order to preserve thermo-labile compounds, low temperature conditions are used throughout the process of extraction.

2.2 Defatting of Samples

The lipid fraction of seaweed is known to vary from 1 to 5% of the algal dry matter, which can be dominated by polyunsaturated fatty acids. Brown and red seaweeds are particularly rich in long chain polyunsaturated fatty acids such as eicosapentaenoic acid (n3, C20:5), while green seaweeds may possess a level of alpha linoleic acid (n3, C18:3). Since these polyunsaturated fatty acids are extremely susceptible to oxidation, they may result in lipid oxidation products during analysis. In order to eliminate the above oxidative processes that may have an effect on the results, samples were defatted prior to extraction of compounds.

Freeze dried seaweed samples were ground into a powder and defatted by blending the powder with hexane (1:5, w/v, 5 min) in a Waring blender at ambient temperature. Defatted samples were air-dried, vacuum packed in polyethylene pouches and kept at −20° C. until extraction.

2.3 Crude Extraction

Different solvents or solvent systems can be used for the extraction of compounds. In general, ethanol is commonly used due to its lower toxicity compared to other solvents. Moreover, ethanol extracts have been demonstrated in many studies to have the highest antioxidant activity.

Compounds were extracted into 80% aqueous ethanol at 4° C. for 24 h. The solvent was then removed under a vacuum at 37° C. for 45 to 60 min and the resulting concentrated slurries were lyophilized for 72 to 96 h at −80° C. and $69 \times 10^{-3}$ mbar using a freeze dryer. Dry extracts were weighed (Extract dry weight in g) and stored at −60° C. until preparation for screening.

Extraction yields were calculated and expressed as g of dry extract per g of dry seaweed as per Table 1.

TABLE 1

Extraction Yields

| Species | Seaweed | Date Collection | Location | Exract dry weight (g) | Yield (g of dry extract/ g of dry plant) |
|---|---|---|---|---|---|
| Chaetomorpha cannibina (extract # 1 for NC 77) | Green | Jul. 22nd, 2013 | Rocky Hr., NL | 4.88 | 8.0% |
| Chaetomorpha cannibina (extract #2 or NC 107) | Green | Aug. 26, 2014 | Mutton Bay, Quebec | 0.7 | 3.88% |

Example 3. Anti-Cancer Screening of Seaweed Crude Extracts 3.1 Purification Through Bioassay-Guided Fractionation Initially, seaweed extracts were evaluated for their anti-cancer activity in in-vitro models via the CIMA assay. From these results, extracts exhibiting the greatest anti-cancer potential were selected for purification via bioassay-guided fractionation.

3.2 Compound Preparation

Stock solutions of the extracts were prepared in dimethylsulfoxide (DMSO) at 10 mg/mL and stored in 200 µl aliquots at −20° C. until analysis. This preparation ensured that the DMSO delivered to cells in culture never exceeded 1%.

3.3 CIMA Assay

Figure 2:
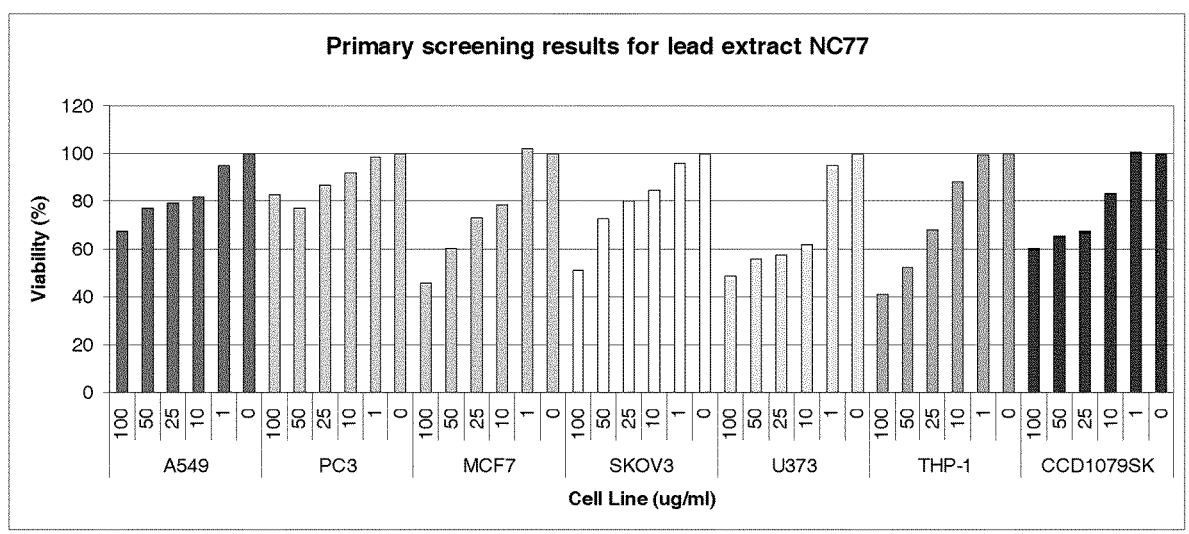
FIG. 2. In vitro activity of different concentrations of crude extracts #1 (NC77) on the viability of seven cell lines.

Prepared extracts were assessed following chronic exposure conditions in which cells were seeded at $2 \times 10^3$ cells/well (96 wells-plate) and incubated with test compounds for 72 h. Each compound was evaluated over a range of concentrations (0, 10, 25, 50 or 100 µg/ml). Cell proliferation was initially assessed using a standard colorimetric indicator of metabolic activity (CIMA) assay. In this assay, tetrazole reduction was evaluated as a measure of metabolic function that evaluates mitochondrial activity to determine the extent of cell proliferation within a culture. This assay is based on the reduction of yellow tetrazolium salt to purple formazan by mitochondrial reductases enzyme in viable cells, resulting in a color changed that confers a change in absorbance. Six human cell lines were selected for primary evaluation: U373 (glioblastoma-astrocytoma), A549 (lung carcinoma), THP-1 (acute monocytic leukemia), MCF7 (mammary gland adenocarcinoma), SKOV3 (ovarian adenocarcinoma), and CCD1079SK (fibroblast, noncancerous but proliferating) (see FIG. 2 and Table 2). Table 3 expresses the $IC_{50}$ for each extract.

From the results presented in Table 2, extract #1 (NC77) was selected for additional fractionation and evaluated in the same manner.

TABLE 2

In vitro screening of fractions #1 (NC77) and #2 (NC107).

| Cell line | (ug/ml) | Extract #1 1 AVG | SD | Extract #2 NC107 AVG | SD |
|---|---|---|---|---|---|
| A549 | 100 | 67.5 | 1.6 | 70.5 | 2.5 |
|  | 50 | 77.1 | 2.4 | 88.8 | 3.2 |
|  | 25 | 78.8 | 3.1 | 91.3 | 3.6 |
|  | 10 | 81.7 | 2.7 | 93.2 | 3.6 |
|  | 1 | 94.6 | 4.6 | 102.5 | 6.8 |
|  | 0 | 100.0 | 0.0 | 100.0 | 0.0 |
|  | DMSO 1% | 92.5 | 3.1 | 92.5 | 3.1 |
|  | SDS 5% | 68.7 | 6.6 | 68.7 | 6.6 |
| PC3 | 100 | 82.5 | 2.2 | 81.1 | 3.0 |
|  | 50 | 77.2 | 4.0 | 87.1 | 2.3 |
|  | 25 | 86.4 | 3.4 | 90.3 | 2.8 |
|  | 10 | 91.7 | 2.0 | 94.9 | 0.8 |
|  | 1 | 98.2 | 1.3 | 97.9 | 5.0 |
|  | 0 | 100.0 | 0.0 | 100.0 | 0.0 |
|  | DMSO 1% | 87.0 | 4.0 | 87.0 | 4.0 |
|  | SDS 5% | 77.3 | 13.3 | 77.3 | 13.3 |
| MCF7 | 100 | 45.6 | 1.0 | 48.7 | 4.5 |
|  | 50 | 60.3 | 2.6 | 71.2 | 4.9 |
|  | 25 | 72.7 | 3.6 | 88.5 | 8.4 |
|  | 10 | 78.7 | 3.9 | 94.0 | 8.5 |
|  | 1 | 101.8 | 12.8 | 102.7 | 3.8 |
|  | 0 | 100.0 | 0.0 | 100.0 | 0.0 |
|  | DMSO 1% | 94.7 | 6.2 | 94.7 | 6.2 |
|  | SDS 5% | 44.1 | 8.0 | 44.1 | 8.0 |
| SKOV3 | 100 | 50.9 | 4.6 | 45.1 | 5.6 |
|  | 50 | 72.3 | 3.7 | 67.8 | 7.4 |
|  | 25 | 79.8 | 4.8 | 76.4 | 5.9 |
|  | 10 | 84.7 | 4.0 | 79.5 | 6.2 |
|  | 1 | 95.5 | 5.7 | 93.6 | 9.5 |
|  | 0 | 100.0 | 0.0 | 100.0 | 0.0 |
|  | DMSO 1% | 95.3 | 7.5 | 95.3 | 7.5 |
|  | SDS 5% | 78.9 | 3.9 | 20.0 | 78.9 |
| U373 | 100 | 48.4 | 2.0 | 34.5 | 3.1 |
|  | 50 | 55.7 | 3.0 | 54.4 | 2.4 |
|  | 25 | 57.0 | 2.8 | 61.3 | 4.4 |
|  | 10 | 61.8 | 4.6 | 76.2 | 4.6 |
|  | 1 | 94.6 | 2.7 | 96.6 | 6.9 |
|  | 0 | 100.0 | 0.0 | 100.0 | 0.0 |
|  | DMSO 1% | 83.4 | 7.7 | 83.4 | 7.7 |
|  | SDS 5% | 48.4 | 6.4 | 48.4 | 6.4 |
| THP-1 | 100 | 40.8 | 1.2 | 35.8 | 1.4 |
|  | 50 | 52.2 | 1.7 | 47.7 | 1.8 |
|  | 25 | 67.9 | 4.4 | 56.6 | 4.8 |
|  | 10 | 88.2 | 3.7 | 82.4 | 9.4 |
|  | 1 | 99.4 | 7.2 | 105.6 | 5.8 |
|  | 0 | 100.0 | 0.0 | 100.0 | 0.0 |
|  | DMSO 1% | 89.2 | 3.6 | 89.2 | 3.6 |
|  | SDS 5% | 20.3 | 4.0 | 20.3 | 4.0 |
| CCD1079SK | 100 | 60.3 | 4.6 | 46.1 | 1.1 |
|  | 50 | 65.5 | 4.5 | 55.7 | 1.4 |
|  | 25 | 67.3 | 3.6 | 62.7 | 2.7 |
|  | 10 | 82.8 | 7.6 | 76.5 | 4.0 |
|  | 1 | 100.3 | 10.3 | 92.8 | 3.1 |
|  | 0 | 100.0 | 0.0 | 100.0 | 0.0 |
|  | DMSO 1% | 91.3 | 7.8 | 91.3 | 7.8 |
|  | SDS 5% | 9.4 | 0.9 | 9.4 | 0.9 |

TABLE 3

$IC_{50}$ calculations for crude extracts NC77 and NC 107

|  | NC77 | NC107 |
|---|---|---|
| A549 | — | — |
| PC3 | — | — |
| MCF7 | 81.9 | 95.9 |

TABLE 3-continued

IC$_{50}$ calculations for crude extracts NC77 and NC 107

| | NC77 | NC107 |
|---|---|---|
| SKOV3 | — | 88.2 |
| U373 | 66.1 | 50.8 |
| THP1 | 75.9 | 45.1 |
| CCD1079SK | — | 86.6 |

— LD$_{50}$ > 1—µg/ml

3.4 Fractionation

Crude extract #1 was fractionated into five fractions by C-18 SPE column separation using 15 ml each of 5% methanol (fraction 1), 25% methanol (fraction 2), 50% methanol (fraction 3), 100% methanol (fraction 4) and methanol:dichloromethane (1:1) (fraction 5). Extracts were fractionated and the resulting fractions were evaluated using CIMA assay. Bio-assay guided fractionation provided detailed information regarding the compound(s) responsible for specific bioactivity.

Figure 3:
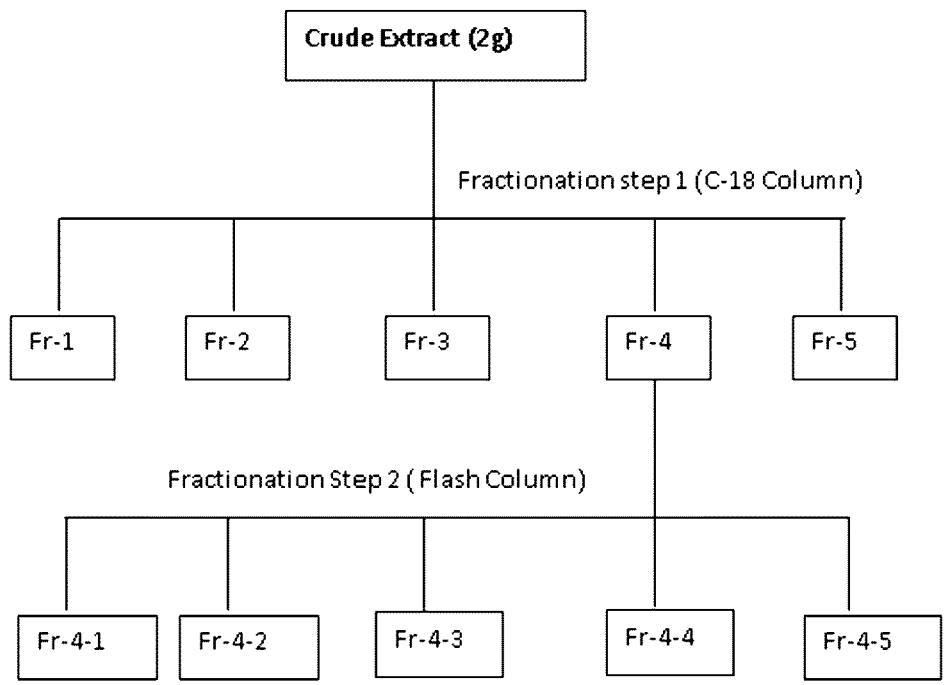
FIG. 3. Fractionation and sub-fractionation strategy for the crude extract #1 of *Chaetomorpha Cannabina* (NC77).

The following amounts were obtained from the strategy described in FIG. 3 and are summarized in Table 4.

TABLE 4

Amounts obtained for each fraction of NC77.

| | Sample (g) |
|---|---|
| Extract 1 | 2.04 |
| F1 | 1.439 |
| F2 | 0.156 |
| F3 | 0.076 |
| F4 | 0.212 |
| F5 | 0.191 |

3.4.1 Fraction Results

The resulting fractions were evaluated using CIMA assay. Bio-assay guided fractionation provided detailed information regarding the compound(s) responsible for specific bioactivity (Table 5). Table 6 indicates the IC$_{50}$ of each fraction.

Figure 4:
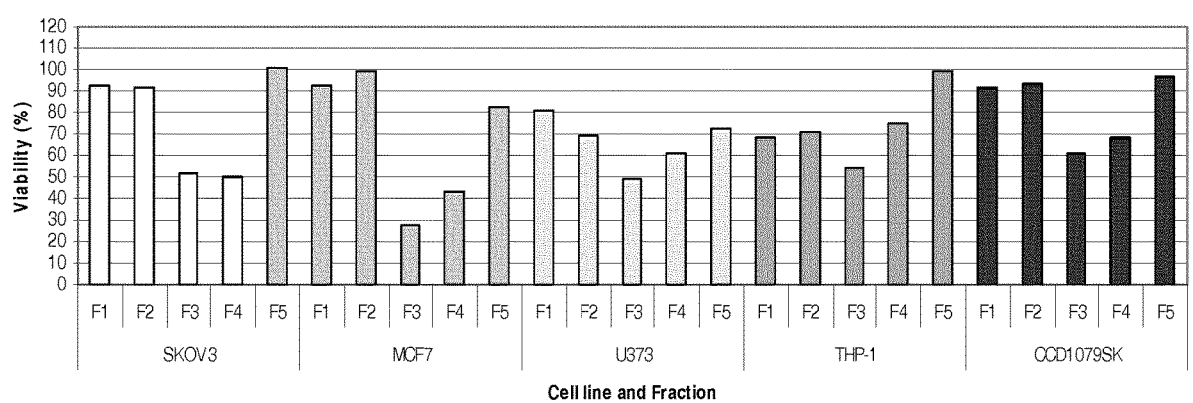
FIG. 4. In vitro activity of fractions (F1-F5) from crude extract #1 (NC77) on viability of five cancer cell lines.

Also shown in FIG. 4, activity was in fractions 3 and 4. Considering the yields obtained for each fraction, the fractionation results clearly indicated that anti-cancer activity was distributed in F4 and priority was established for the selection for extract #1 (fraction 4). Fraction 4 (0.34 g) from NC77 was thus subjected to further sub-fractionation as presented below.

TABLE 5

Identification of active fractions from extract #1

| | | F1 | | F2 | | F3 | | F4 | | F5 | |
|---|---|---|---|---|---|---|---|---|---|---|---|
| Cell line | (ug/ml) | AVG | SD | AVG | SD | AVG | SD | AVG | SD | AVG | SD |
| SKOV3 | 100 | 92.4 | 8.9 | 91.4 | 2.3 | 51.3 | 7.0 | 50.1* | 5.8 | 100.8 | 10.8 |
| | 50 | 104.2 | 12.5 | 92.6 | 3.5 | 77.0 | 11.0 | 53.8# | 3.4 | 96.3 | 4.3 |
| | 25 | 100.0 | 6.3 | 94.0 | 0.6 | 87.5 | 9.7 | 60.7* | 6.2 | 95.1 | 12.1 |
| | 10 | 101.0 | 11.1 | 99.5 | 3.9 | 91.4 | 10.9 | 68.3* | 4.7 | 93.9 | 12.9 |
| | 1 | 103.6 | 8.2 | 102.3 | 5.3 | 100.9 | 12.3 | 95.0 | 2.5 | 108.4 | 9.9 |
| | 0 | 100.0 | 0.0 | 100.0 | 0.0 | 100.0 | 0.0 | 100.0 | 0.0 | 100.0 | 0.0 |
| | DMSO 1% | 88.6 | 3.7 | 88.6 | 3.7 | 88.6 | 3.7 | 88.6 | 3.7 | 88.6 | 3.7 |
| | SDS 5% | 56.5 | 5.4 | 56.5 | 5.4 | 56.5 | 5.4 | 56.5 | 5.4 | 56.5 | 5.4 |
| MCF7 | 100 | 92.6 | 11.2 | 98.8 | 4.4 | 27.8 | 2.5 | 43.2# | 5.4 | 82.3 | 2.5 |
| | 50 | 98.4 | 4.9 | 99.4 | 7.3 | 52.5 | 6.2 | 50.3* | 3.0 | 91.1 | 2.9 |
| | 25 | 105.8 | 6.4 | 100.0 | 2.8 | 92.9 | 8.2 | 73.3* | 7.9 | 96.7 | 7.5 |
| | 10 | 103.4 | 2.2 | 106.8 | 5.4 | 101.1 | 4.2 | 80.4 | 15.2 | 96.0 | 3.7 |
| | 1 | 103.3 | 6.4 | 101.1 | 3.6 | 105.7 | 4.7 | 97.1 | 11.3 | 98.9 | 2.9 |
| | 0 | 100.0 | 0.0 | 100.0 | 0.0 | 100.0 | 0.0 | 100.0 | 0.0 | 100.0 | 0.0 |
| | DMSO 1% | 92.1 | 5.9 | 92.1 | 5.9 | 92.1 | 5.9 | 92.1 | 5.9 | 92.1 | 5.9 |
| | SDS 5% | 49.9 | 5.6 | 49.9 | 5.6 | 49.9 | 5.6 | 49.9 | 5.6 | 49.9 | 5.6 |
| U373 | 100 | 81.1 | 3.6 | 69.0 | 6.3 | 49.2 | 3.1 | 60.7 | 4.2 | 72.2 | 1.9 |
| | 50 | 85.3 | 8.4 | 82.3 | 5.9 | 83.0 | 5.8 | 87.2 | 5.4 | 84.4 | 3.1 |
| | 25 | 85.4 | 9.2 | 92.1 | 7.9 | 102.6 | 9.2 | 93.4 | 6.9 | 90.3 | 2.0 |
| | 10 | 103.9 | 6.3 | 103.2 | 10.1 | 102.2 | 8.1 | 93.6 | 7.0 | 106.0 | 2.6 |
| | 1 | 103.1 | 12.3 | 101.6 | 8.2 | 97.8 | 6.2 | 103.2 | 14.9 | 117.7 | 7.4 |
| | 0 | 100.0 | 0.0 | 100.0 | 0.0 | 100.0 | 0.0 | 100.0 | 0.0 | 100.0 | 0.0 |
| | DMSO 1% | 94.7 | 6.2 | 94.7 | 6.2 | 94.7 | 6.2 | 94.7 | 6.2 | 94.7 | 6.2 |
| | SDS 5% | 44.1 | 8.0 | 44.1 | 8.0 | 44.1 | 8.0 | 44.1 | 8.0 | 44.1 | 8.0 |
| THP-1 | 100 | 68.1 | 0.9 | 70.8 | 4.1 | 54.3 | 1.7 | 74.9 | 3.7 | 98.8 | 9.5 |
| | 50 | 79.5 | 3.2 | 78.2 | 8.4 | 75.5 | 4.1 | 78.8 | 4.1 | 99.1 | 10.9 |
| | 25 | 74.5 | 3.1 | 80.0 | 4.9 | 75.6 | 5.0 | 79.1 | 5.8 | 92.4 | 8.6 |
| | 10 | 75.9 | 3.7 | 78.9 | 5.1 | 75.0 | 3.1 | 81.3 | 3.2 | 93.2 | 7.5 |
| | 1 | 75.7 | 1.8 | 80.4 | 3.5 | 82.7 | 5.9 | 87.0 | 7.8 | 93.9 | 5.6 |
| | 0 | 100.0 | 0.0 | 100.0 | 0.0 | 100.0 | 0.0 | 100.0 | 0.0 | 100.0 | 0.0 |
| | DMSO 1% | 103.3 | 6.2 | 103.3 | 6.2 | 103.3 | 6.2 | 103.3 | 6.2 | 103.3 | 6.2 |
| | SDS 5% | 36.2 | 4.6 | 36.2 | 4.6 | 36.2 | 4.6 | 36.2 | 4.6 | 36.2 | 4.6 |
| CCD1079SK | 100 | 91.9 | 4.5 | 93.3 | 8.8 | 60.6 | 8.4 | 68.1 | 6.7 | 96.6 | 4.1 |
| | 50 | 102.4 | 8.2 | 103.0 | 12.1 | 85.6 | 8.6 | 76.8 | 6.0 | 100.1 | 4.5 |
| | 25 | 99.3 | 1.5 | 101.8 | 11.5 | 85.8 | 13.8 | 81.2 | 3.4 | 98.8 | 6.2 |
| | 10 | 100.7 | 5.1 | 99.5 | 13.5 | 93.8 | 8.1 | 84.0 | 1.5 | 96.9 | 5.1 |
| | 1 | 102.7 | 4.4 | 98.3 | 9.8 | 97.3 | 10.9 | 89.2 | 4.7 | 98.5 | 1.9 |
| | 0 | 100.0 | 0.0 | 100.0 | 0.0 | 100.0 | 0.0 | 100.0 | 0.0 | 100.0 | 0.0 |
| | DMSO 1% | 87.2 | 9.7 | 87.2 | 9.7 | 87.2 | 9.7 | 87.2 | 9.7 | 87.2 | 9.7 |
| | SDS 5% | 11.3 | 0.6 | 11.3 | 0.6 | 11.3 | 0.6 | 11.3 | 0.6 | 11.3 | 0.6 |

TABLE 6

IC$_{50}$ calculations for NC77 fractions

| | NC77 | | | | |
|---|---|---|---|---|---|
| | F1 | F2 | F3 | F4 | F5 |
| SKOV3 | — | — | — | 80.2 | — |
| MCF7 | — | — | 67.9 | 73.9 | — |
| U373 | — | — | — | — | — |
| THP-1 | — | — | — | — | — |
| CCD1079SK | — | — | — | — | — |

—, LD50 > 100 µg/ml

Example 4. Sub-Fractionation of Fraction 4 from Extract #1 (NC77)

Fraction 4 was selected for further sub-fractionation based on the bioassay results (Table 5). Thus, in a second stage, NC77-F4 was dissolved in dichloromethane/methanol and mixed with Celite and dried via rotary evaporation. The sample was loaded on 24 g Teledyne ISCO High Performance GOLD silica gel column and eluted with dichloromethane/methanol on CombiFlash® Rf, Teledyne ISCO. Sub-fractionation was conducted as a gradient of Solvent A (CH$_2$Cl$_2$) and Solvent B (1:1 methanol: water) as follows: 0% B for 2 CV (column volume) then to 40% B for 17 CV, to 100% B for 4 CV for a total elution in 23 CV.

Fractions were monitored by TLC and some were combined and dried using Rotavap and Genevac to yield five (5) sub-fractions as presented in Table 7.

TABLE 7

Yields of sub-fractionation of NC77-F4

| Sample | Sample weight (g) | Fr. 1 (g) | Fr. 2 (g) | Fr. 3 (g) | Fr. 4 (g) | Fr. 5 (g) |
|---|---|---|---|---|---|---|
| NC77 - Fr. 4 | 0.21 | 0.011 | 0.044 | 0.006 | 0.036 | 0.064 |

These sub-fractions were again subjected to the bioassay evaluation presented above. Results are expressed in Table 8 as % viability (means±standard deviation of three replicates), with LD$_{50}$/IC$_{50}$ values in Table 9. The most active results are shaded in grey with statistical analyses indicated. The maximum DMSO concentration was 1% at 100 µg/ml with 5% SDS used as a known toxic inducer.

Results clearly indicated that anti-cancer activity was distributed in sub-fractions F3 and F4 from fraction 4 of NC77.

TABLE 8

In vitro screening results - sub-fractions from NC77-Fraction 4

| | | NC77 | | | | | | | | | |
|---|---|---|---|---|---|---|---|---|---|---|---|
| | | F1 | | F2 | | F3 | | F4 | | F5 | |
| Cell line | (ug/ml) | AVG | SD | AVG | SD | AVG | SD | AVG | SD | AVG | SD |
| PC3 | 100 | 104.4 | 3.4 | 92.4 | 4.2 | 89.7 | 6.8 | 98.9 | 6.0 | 87.9 | 2.6 |
| | 50 | 116.2 | 21.2 | 93.3 | 7.3 | 93.3 | 8.3 | 93.2 | 6.1 | 89.3 | 3.9 |
| | 25 | 120.9 | 13.8 | 97.6 | 8.6 | 97.9 | 9.0 | 98.4 | 1.9 | 95.0 | 4.5 |
| | 10 | 115.4 | 9.5 | 99.6 | 8.5 | 99.3 | 6.1 | 101.4 | 3.5 | 96.1 | 6.0 |
| | 1 | 120.9 | 14.2 | 96.7 | 10.9 | 101.7 | 9.9 | 101.6 | 8.0 | 105.5 | 3.4 |
| | 0 | 100.0 | 0.0 | 100.0 | 0.0 | 100.0 | 0.0 | 100.0 | 0.0 | 100.0 | 0.0 |
| | DMSO 1% | 7.7 | 0.8 | 7.7 | 0.8 | 7.7 | 0.8 | 7.7 | 0.8 | 7.7 | 0.8 |
| | SDS 5% | 94.4 | 6.1 | 94.4 | 6.1 | 94.4 | 6.1 | 94.4 | 6.1 | 94.4 | 6.1 |
| SKOV3 | 100 | 91.0 | 8.2 | 91.2 | 4.4 | 86.6 | 1.9 | 92.0 | 8.0 | 84.6 | 2.6 |
| | 50 | 97.7 | 0.8 | 102.8 | 2.2 | 95.3 | 2.1 | 101.7 | 3.9 | 86.7 | 2.6 |
| | 25 | 100.0 | 1.3 | 103.3 | 1.7 | 100.0 | 4.5 | 103.2 | 2.0 | 86.1 | 4.5 |
| | 10 | 99.0 | 3.8 | 102.2 | 0.7 | 99.8 | 0.9 | 101.2 | 4.0 | 91.0 | 1.6 |
| | 1 | 98.1 | 1.3 | 103.6 | 2.6 | 100.5 | 6.5 | 99.7 | 1.0 | 97.0 | 3.6 |
| | 0 | 100.0 | 0.0 | 100.0 | 0.0 | 100.0 | 0.0 | 100.0 | 0.0 | 100.0 | 0.0 |
| | DMSO 1% | 14.3 | 0.7 | 14.3 | 0.7 | 14.3 | 0.7 | 14.3 | 0.7 | 14.3 | 0.7 |
| | SDS 5% | 90.7 | 33.4 | 90.7 | 33.4 | 90.7 | 33.4 | 90.7 | 33.4 | 90.7 | 33.4 |
| A549 | 100 | 100.1 | 11.7 | 109.9 | 12.7 | 88.7 | 12.2 | 98.2 | 11.1 | 88.2 | 5.4 |
| | 50 | 107.9 | 3.7 | 103.3 | 10.5 | 99.7 | 10.7 | 110.6 | 2.3 | 83.0 | 4.6 |
| | 25 | 110.8 | 5.4 | 105.9 | 5.1 | 104.6 | 9.5 | 117.5 | 3.7 | 81.6 | 7.1 |
| | 10 | 112.9 | 2.1 | 109.5 | 5.0 | 106.3 | 9.6 | 117.1 | 12.1 | 94.5 | 11.9 |
| | 1 | 106.1 | 4.0 | 112.8 | 12.5 | 105.0 | 6.0 | 117.4 | 5.6 | 94.7 | 8.7 |
| | 0 | 100.0 | 0.0 | 100.0 | 0.0 | 100.0 | 0.0 | 100.0 | 0.0 | 100.0 | 0.0 |
| | DMSO 1% | 6.4 | 0.6 | 6.4 | 0.6 | 6.4 | 0.6 | 6.4 | 0.6 | 6.4 | 0.6 |
| | SDS 5% | 66.2 | 13.3 | 66.2 | 13.3 | 66.2 | 13.3 | 66.2 | 13.3 | 66.2 | 13.3 |
| THP-1 | 100 | 11.0 | 0.5 | 12.5 | 1.2 | 15.0 | 1.6 | 27.2 | 4.0 | 19.1 | 2.0 |
| | 50 | 37.5 | 1.9 | 39.3 | 1.1 | 26.9 | 3.6 | 57.1 | 4.7 | 59.8 | 8.6 |
| | 25 | 61.9 | 1.4 | 71.8 | 5.9 | 66.5 | 8.3 | 67.5 | 2.2 | 85.5 | 5.5 |
| | 10 | 99.1 | 5.1 | 78.0 | 8.9 | 72.9 | 9.2 | 76.3 | 4.5 | 87.9 | 6.1 |
| | 1 | 102.2 | 10.6 | 96.8 | 8.6 | 104.3 | 12.7 | 78.2 | 7.2 | 96.5 | 5.0 |
| | 0 | 100.0 | 0.0 | 100.0 | 0.0 | 100.0 | 0.0 | 100.0 | 0.0 | 100.0 | 0.0 |
| | DMSO 1% | 1.0 | 0.5 | 1.0 | 0.5 | 1.0 | 0.5 | 1.0 | 0.5 | 1.0 | 0.5 |
| | SDS 5% | 39.9 | 2.9 | 39.9 | 2.9 | 39.9 | 2.9 | 39.9 | 2.9 | 39.9 | 2.9 |
| U373 | 100 | 6.0 | 1.4 | 3.3 | 0.8 | 1.4 | 0.5 | 28.1 | 3.5 | 5.3 | 0.7 |
| | 50 | 79.6 | 8.4 | 109.0 | 14.2 | 43.4 | 7.0 | 67.4 | 4.5 | 61.5 | 9.4 |
| | 25 | 92.5 | 30.1 | 113.0 | 2.9 | 88.2 | 5.5 | 72.1 | 2.0 | 66.0 | 8.5 |
| | 10 | 108.4 | 18.5 | 102.6 | 9.6 | 103.3 | 13.8 | 76.1 | 4.1 | 88.7 | 8.2 |
| | 1 | 106.1 | 14.8 | 117.6 | 5.4 | 110.5 | 7.3 | 95.9 | 3.0 | 81.0 | 9.5 |
| | 0 | 100.0 | 0.0 | 100.0 | 0.0 | 100.0 | 0.0 | 100.0 | 0.0 | 100.0 | 0.0 |
| | DMSO 1% | 3.0 | 0.4 | 3.0 | 0.4 | 3.6 | 0.4 | 3.0 | 0.4 | 3.0 | 0.4 |
| | SDS 5% | 78.5 | 11.6 | 78.5 | 11.6 | 78.5 | 11.6 | 78.5 | 11.6 | 78.5 | 11.6 |

TABLE 8-continued

In vitro screening results - sub-fractions from NC77-Fraction 4

| | | NC77 | | | | | | | | | |
|---|---|---|---|---|---|---|---|---|---|---|---|
| | | F1 | | F2 | | F3 | | F4 | | F5 | |
| Cell line (ug/ml) | | AVG | SD | AVG | SD | AVG | SD | AVG | SD | AVG | SD |
| CCD1079SK | 100 | 22.5 | 3.1 | 8.2 | 0.9 | 9.4 | 1.9 | 32.9 | 1.8 | 66.6 | 13.3 |
| | 50 | 54.2 | 0.5 | 89.4 | 6.7 | 9.3 | 3.5 | 60.3 | 4.6 | 82.6 | 6.1 |
| | 25 | 89.8 | 1.8 | 95.5 | 2.7 | 58.1 | 5.2 | 81.1 | 8.6 | 76.3 | 7.5 |
| | 10 | 94.0 | 4.7 | 98.1 | 11.2 | 85.2 | 8.9 | 86.2 | 4.7 | 98.7 | 11.6 |
| | 1 | 101.5 | 4.8 | 95.6 | 0.9 | 101.7 | 8.7 | 98.8 | 6.9 | 96.3 | 4.1 |
| | 0 | 100.0 | 0.0 | 100.0 | 0.0 | 100.0 | 0.0 | 100.0 | 0.0 | 100.0 | 0.0 |
| | DMSO 1% | 8.6 | 0.9 | 8.6 | 0.9 | 8.6 | 0.9 | 8.6 | 0.9 | 8.6 | 0.9 |
| | SDS 5% | 87.9 | 7.2 | 87.9 | 7.2 | 87.9 | 7.2 | 87.9 | 7.2 | 87.9 | 7.2 |
| MCF7 | 100 | 23.1 | 2.9 | 24.1 | 0.5 | 26.7 | 2.0 | 25.1 | 1.7 | 57.5 | 7.3 |
| | 50 | 42.3 | 3.7 | 69.3 | 3.2 | 56.4 | 8.1 | 45.2 | 4.6 | 103.6 | 12.1 |
| | 25 | 83.7 | 9.0 | 92.5 | 2.3 | 84.3 | 8.4 | 81.8 | 5.1 | 108.6 | 4.0 |
| | 10 | 93.6 | 7.2 | 91.4 | 1.2 | 101.0 | 11.8 | 84.3 | 0.5 | 104.3 | 6.8 |
| | 1 | 96.7 | 2.6 | 98.6 | 6.6 | 98.7 | 9.0 | 87.3 | 3.3 | 107.3 | 4.7 |
| | 0 | 100.0 | 0.0 | 100.0 | 0.0 | 100.0 | 0.0 | 100.0 | 0.0 | 100.0 | 0.0 |
| | DMSO 1% | 16.9 | 3.3 | 16.9 | 3.3 | 16.9 | 3.3 | 16.9 | 3.3 | 16.9 | 3.3 |
| | SDS 5% | 93.7 | 8.7 | 93.7 | 8.7 | 93.7 | 8.7 | 93.7 | 8.7 | 93.7 | 8.7 |

TABLE 9

$LD_{50}$ calculations sub-fractions from NC77-F4 (µg/ml)

| Cell line (ug/ml) | F1 | F2 | F3 | F4 | F5 |
|---|---|---|---|---|---|
| PC3 | — | — | — | — | — |
| SKOV3 | — | — | — | — | — |
| A549 | — | — | — | — | — |
| THP-1 | 31.1 | 48.8 | 34.0 | 58.8 | 62.3 |
| U373 | 68.6 | — | 49.1 | 66.9 | 50.4 |
| CCD1079SK | 64.3 | — | 22.2 | 71.1 | — |
| MCF7 | 59.4 | 70.4 | 58.1 | 50.6 | — |

Example 5. Characterization of a Main Component from NC77 and NC77-F4

5.1. Sample Preparation and Analysis:
FAME Preparation and GC-MS Analysis

Extract #1 (NC77) and its fraction-4 (NC77-Fr. 4) were analyzed by GC-MS. Samples were added 1 mL sodium methoxide solution and 1 mL hexane, with cap closed. The reaction vials were put in a heating block (80° C.) for 15 min shaking vials with hand at 5 min intervals. Added 1 mL saturated NaCl solution after cooling to room temperature and shaken by hand several times. The reaction vials were then centrifuged for 20 min at 2,000 rpm. The upper solutions were transfer to GC vials. For GC-MS analysis, Agilent 6890 with 5973 Mass Selective Detector were used. The column was Agilent DB-23 (59 m×0.25 mm, 0.15 µm), injection volume 1 µL. Oven program: 50° C. for 1 min, 25° C./min to 170° C., 2.75° C./min to 215° C. (hold 12 min), 40° C./min to 230° C. (hold 3.11 min). Total runtime was 37.65 min. FID temperature was 280° C., hydrogen flow 40 mL/min, air flow 400 mL/min, makeup flow N2 20 mL/min. Split ratio was 2:1. Carrier gas was helium and kept at constant pressure (30 psi). MSD ionization mode was EI. interface temperature 250° C., MS source 230° C., MS Quad 150° C. Mass range was 50-600 m/z.

HPLC-DAD Analysis to Compare Different Batches

The separation was conducted on an Agilent Zorbax SB-C18 (2.1×30 mm 3.5 µm) column using Agilent HPLC 1100. Solvent A was 10 mM ammonium formate (pH 3.2) and solvent B was 90% acetonitrile with 10% 100 mM ammonium formate (pH3.2). Gradient was 30% B to 100% B in 12 min and wash with acetonitrile with 0.1% formic acid for 2 min. Column temperature was 55° C. Flow rate was 0.5 mL/min.

HPLC-DAD/MS Analysis of Carotenoids

Analysis was done on Agilent 1200 system using YMC carotenoid column, 0.5 µm (250×2 mm) at 32° C. Mobile phase: solvent A 50 mM AmAc/MeOH, Solvent B MTBE, with gradient of 5-65% B in 40 min. Flow rate was 0.2 mL/min, and DAD detector monitored at 450 nm. Identification of peaks in the chromatogram was made on the basis of RT comparison to known standards: fucoxanthin, astaxanthin, lutein, zeaxanthin, canthaxanthin, α-& β-Carotene. All standards were purchased from Chromadex.

UPLC-DAD/ELSD/HRMS and MS/MS

The following instruments were used for LC-UV-ELSD-HRMS data acquisition: Accela 1250 pump (Thermo Fisher Scientific); Exactive benchtop Orbitrap mass spectrometer (Thermo Fisher) equipped with heated electrospray ionization probe; Utimate 3000 DAD (Thermo Scientific Dionex) and ELSD 3300 (Alltech). Separation was carried out on a Hypersil C18 column (50×2.1 mm, Thermo) using mobile phase consisted of (A) 0.1% formic acid and (B) 0.1% formic acid in acetonitrile, with a linear gradient from 5% B to 100% B in 4.2 min, held for 3.2 min, flow-rate was at 400 µL/min.

HRMS was acquired in positive or negative polarity at 25,000 resolution, each with a HCD scan with collision energy at 50 eV for all-ion-fragmentations with 10,000 resolution. The following optimal ion source conditions were used: sheath flow is 15, auxiliary gas flow rate of 3; spray voltage of 3 kV (−2.5 kV for negative); capillary and heater temperature of 350° C. and 250° C., respectively.

NMR

The samples were reconstituted in 100 µL of $CDCl_3$ and 60 µL of each sample was transferred to 1.7 mm NMR tubes. All spectra were run on a Bruker Avance III 700 MHz spectrometer equipped with a 1.7 mm cryogenically cooled probe operating at 16K.

5.2. Analysis of NC77 and NC77-Fr. 4

The preliminary profiling work done previously indicated that lipids were the main components in NC77-Fr. 4. As such, GC-MS analysis was performed to understand the fatty acids composition in this extract and its bioactive fraction.

Figure 5:
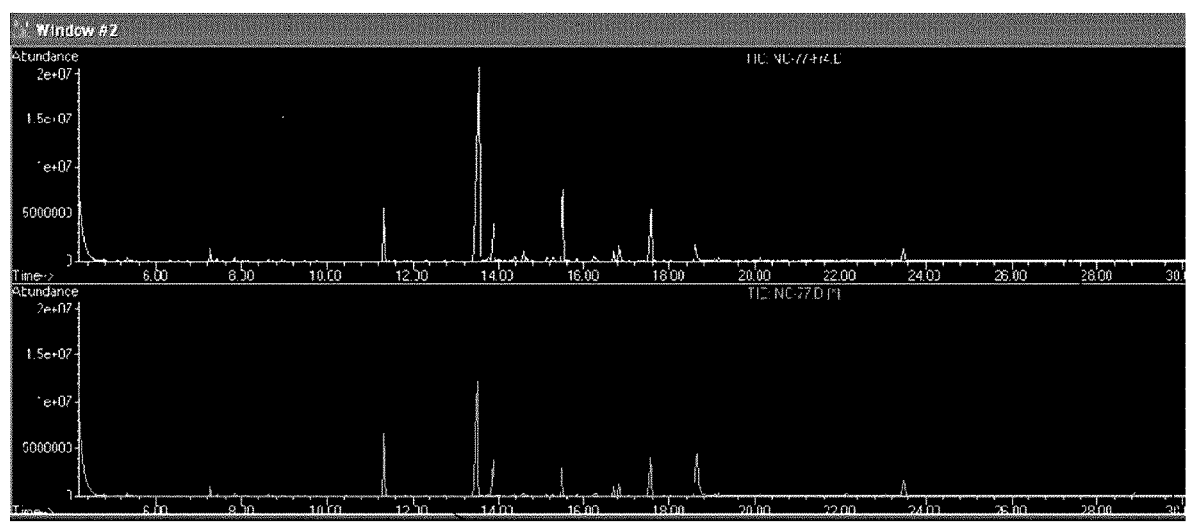
FIG. 5. GC chromatogram of FAME prepared from NC77 and NC77-Fr-4 fraction.

FIG. 5 is the GC chromatogram of FAME prepared from extract #1 (NC77) and #1-F4 (NC77-Fr. 4). The retention time and tentative identification based on NIST database matching are presented in Table 10. The major fatty acid was shown to be palmitic acid.

TABLE 10

Identification of fatty acids using GC-MS analysis of extract #1 (NC77) and extract #1-F4 (NC77-Fr. 4)

| RT (min) | Compounds |
|---|---|
| 11.32 | Methyl tetradecanoate |
| 13.51 | Hexadecanoic acid, methyl ester |
| 13.87 | 9-Hexadecenoir acid, methyl ester, (Z)- |
| 15.49 | unknown |
| 16.71 | 8-Octadecenoic acid, methyl ester |
| 16.83 | 8-Octadecenoic acid, methyl ester |
| 17.56 | 9, 12-Octadecadienoic acid (Z, Z)-, methyl ester |
| 18.66 | 1,2-15, 16-Diepoxyhexadecane |
| 23.47 | Methyl eicosa-5, 8, 11, 14, 17-pentaenoate (EPA) |

We also compared the NMR and HPLC profiles of two different batches of NC77 and NC77-Fr. 4 prepared and tested earlier, with new samples.

Figure 6:
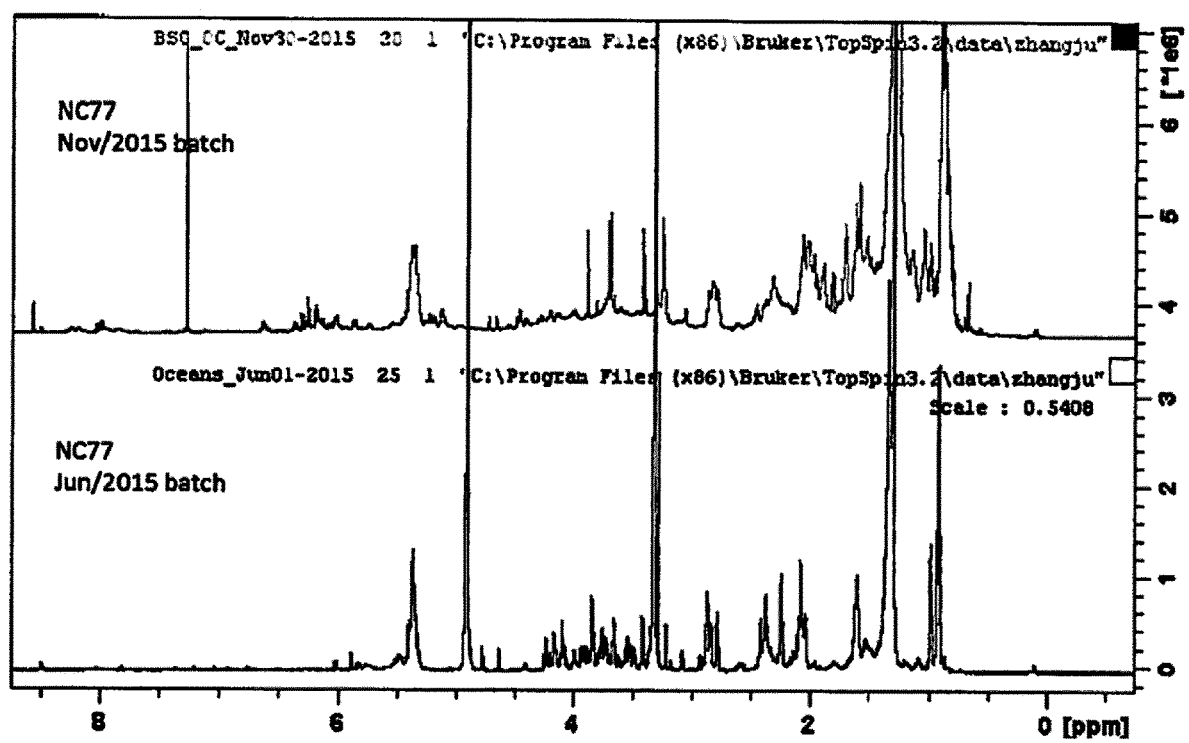
FIG. 6. $^1$H-NMR profile for NC77 extract.
Figure 7:
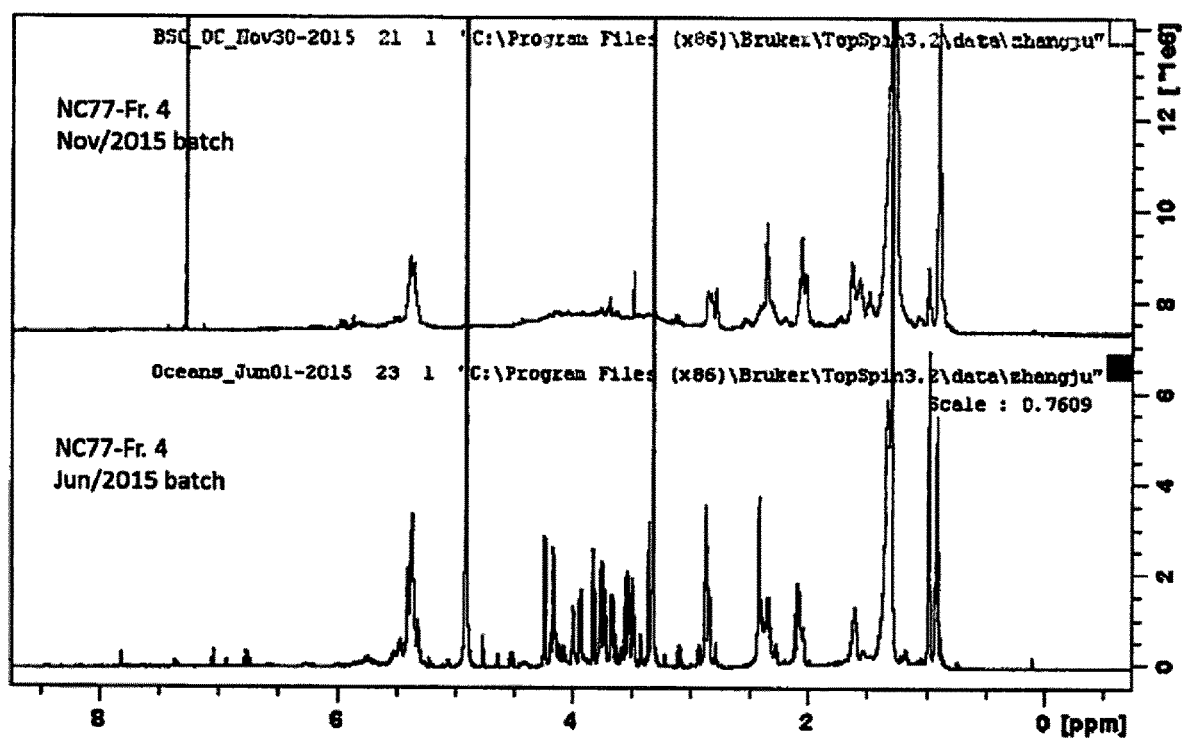
FIG. 7. $^1$H-NMR profiles for NC77-Fr-4 fraction.

As shown in FIGS. 6 and 7, extract #1 and its fraction 4 (NC77 and NC77-Fr. 4) prepared in November 2015 have similar $^1$H-NMR profiles as the ones observed from the earlier batch (June/2015). Lipids (fatty acid) appeared to be the major components.

Figure 8:
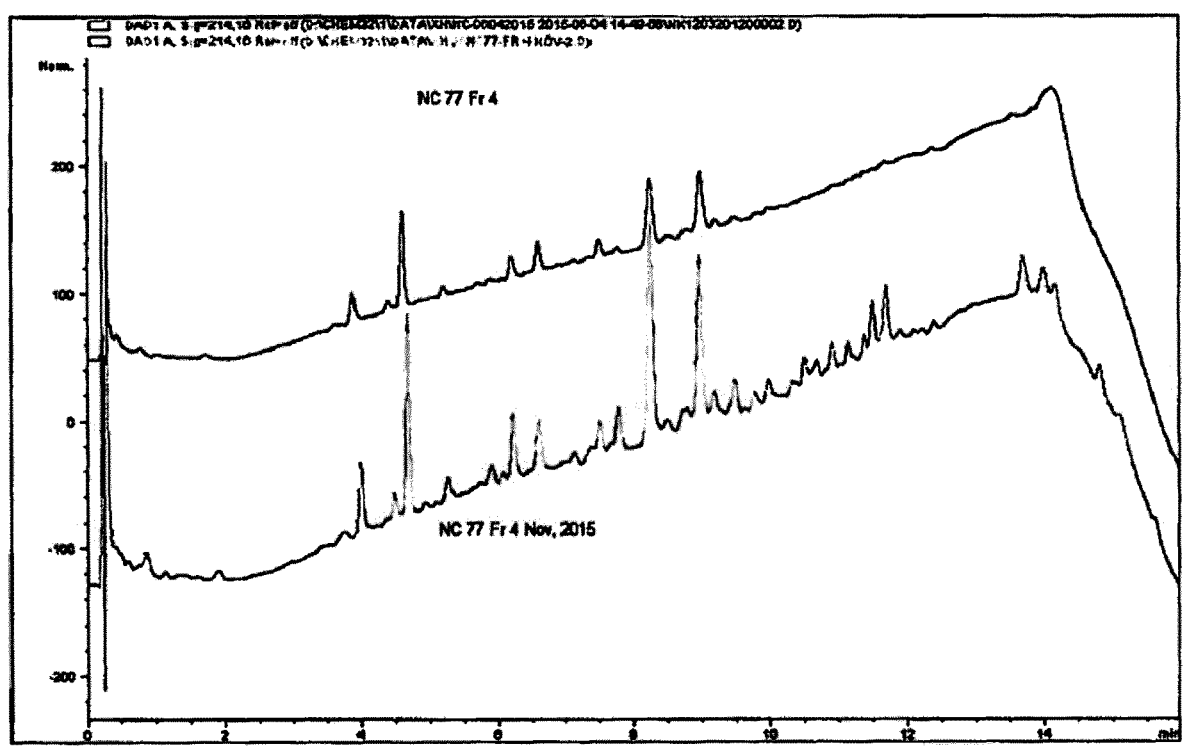
FIG. 8. HPLC comparison between two samples of NC77-Fr4 from two different harvesting dates.

HPLC comparison is shown in FIG. 8. The two appeared to have similar profiles of main components.

Example 6. Fractionation and Purification of Main Components from NC77-F4-F13

In a second series of experiments, NC77 was fractionated as above and fraction 4 was sub-fractioned but with a slightly different protocol to obtain better compound separation. In short, 3.14 g of extract #1 (NC77) was dissolved in methanol, mixed on Celite and dried using Rotavap. The sample was then loaded on pre-conditioned and equilibrated Thermo Scientific SPE column (HYPERSEP C18 20 G). Four fractions were obtained by eluting the SPE column with 5% methanol (Fr. 1), 25% methanol (Fr. 2), 50% methanol (Fr. 3) and 100% methanol (Fr. 4).

Based on previous bioassay result, fraction-4 (0.34 g) was subjected to further fractionation. Fraction 4 was dissolved in dichloromethane/methanol and mixed with Celite and dried. The sample was loaded on 24 g Teledyne ISCO High Performance GOLD silica gel column and eluted with dichloromethane/methanol on CombiFlash® Rf, Teledyne ISCO. The eluting solvent gradient (A and B) was as the following: 0% B for 2 CV (column volume) then to 40% B for 15 CV and kept at 40% B for 2 CV, to 100% B for 2 CV and kept at 100% B for 2 CV. Total elution volume was 23 CV. A is dichloromethane and B is methanol/dichloromethane (1:1). Fractions were monitored by TLC and some combined and dried using Rotavap and Genevac.

Based on TLC analysis, sub-fraction 13 of Fr. 4 (Fr. 4-13, 0.11 g) was chosen for subsequent purification as it showed to contain major components. In this step, 12 g silica gel column by CombiFlash® Rf was used. The solvent (A and B) gradient was: 0% B for 2 CV then to 100% B for 25 CV and kept at 100% B for 2 CV. The total elution was 29 CV. A is dichloromethane and B is 5% methanol in dichloromethane. Again, fractions were selectively combined according to TLC.

Three sub-fractions were further purified using semi preparative HPLC (Agilent). The column used was ZORBAX SB-C18 (9.4×50 mm, 5 μm) and the mobile phase was water/acetonitrile. Eluting gradient varied for different samples so to optimize separation. The column temperature was at 55° C. and flow rate 5 mL/min.

Figure 9:
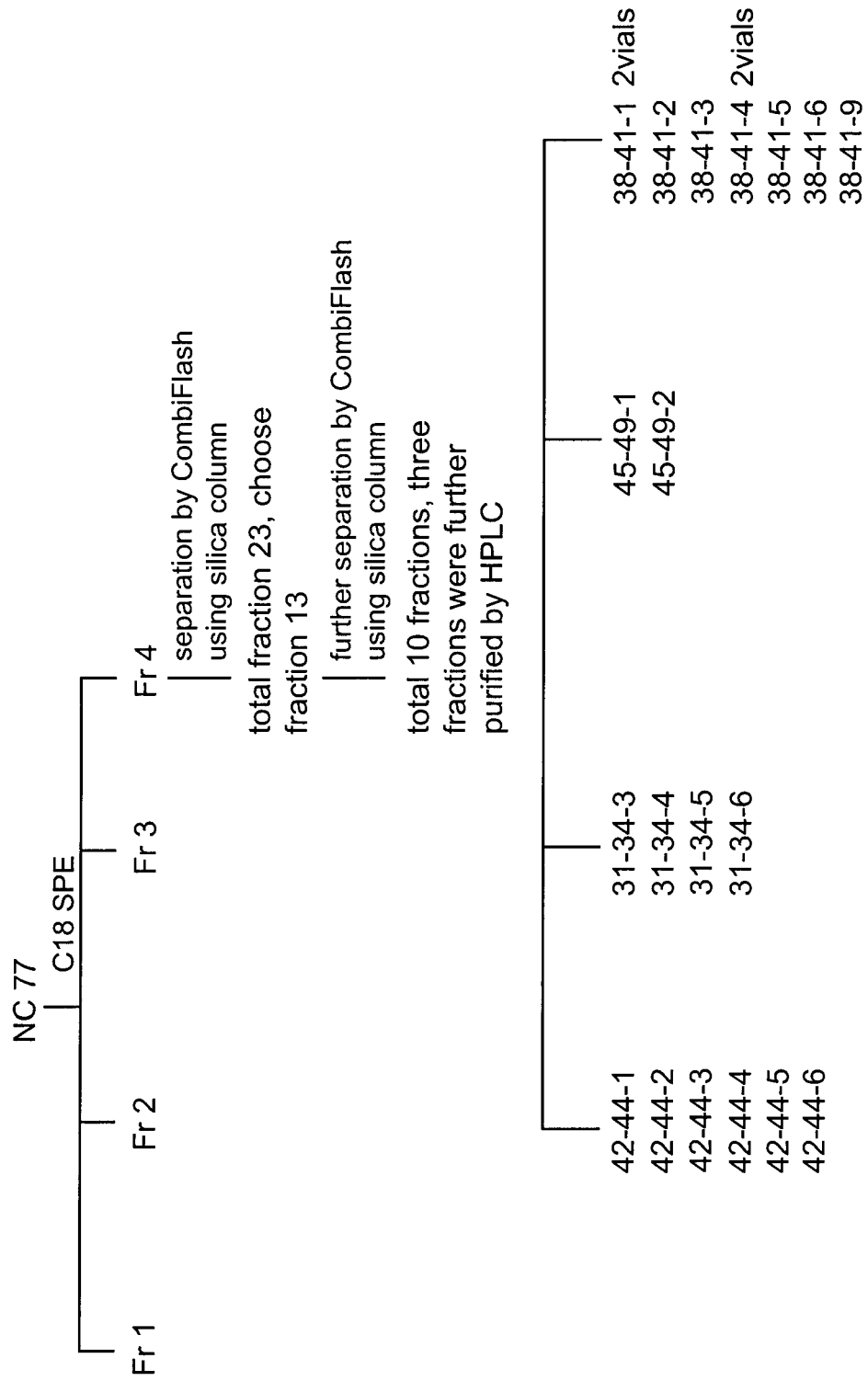
FIG. 9. Flowchart of fractionation, sub-fractionation and purification of main components from NC77.

As shown in FIG. 9, the above described fractionation and purification yielded 19 samples for full structural analysis. Among them, sample 31-34-5 (3.9 mg) was a pure compound.

Example 7. Structure of Pure Compound 31-34-5

7.1. Compound 31-34-5 (Formula (I))

Figure 10:
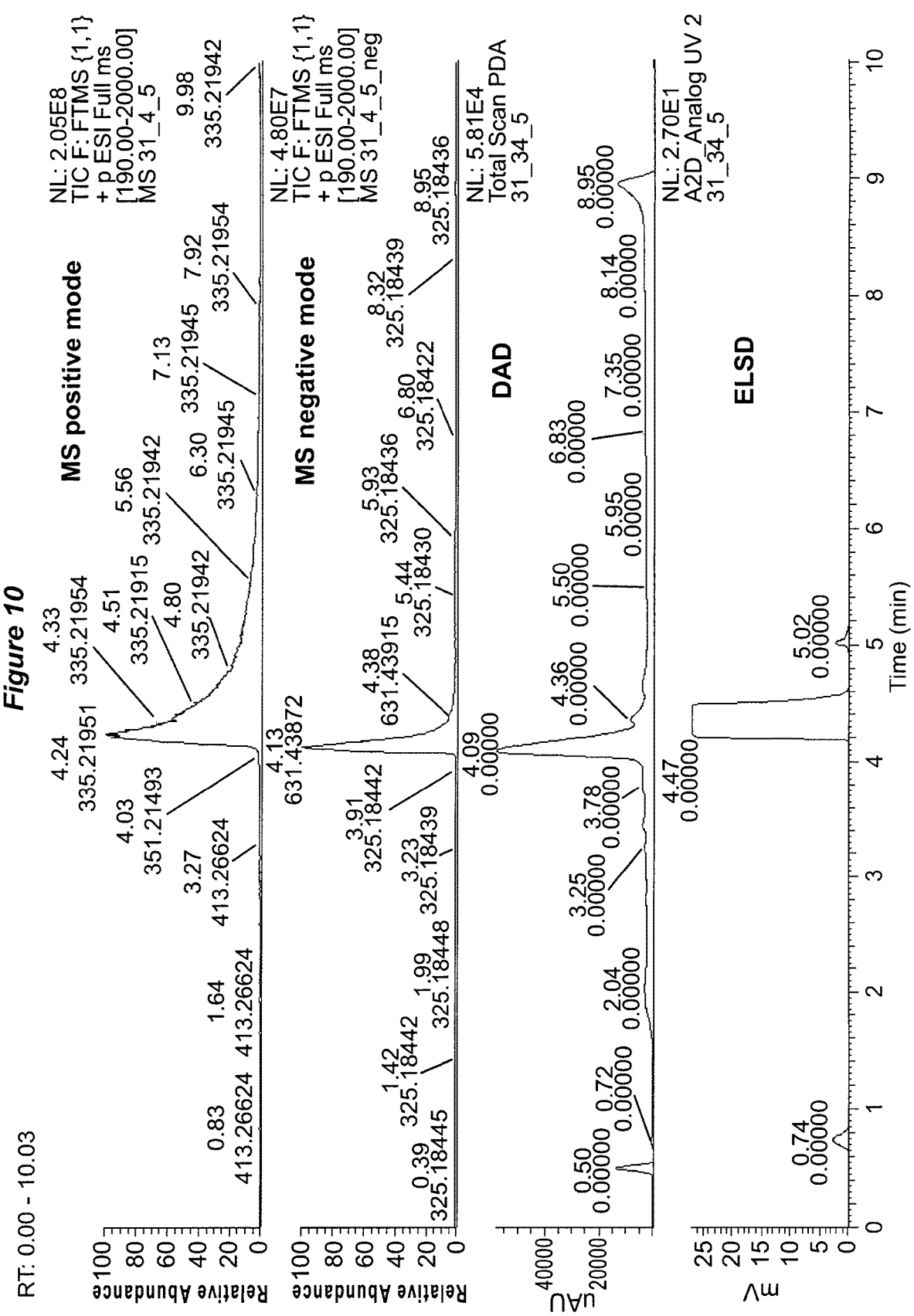
FIG. 10. UPLC-DAD/ELSD/HRMS profile of compound of formula (I).
Figure 11:
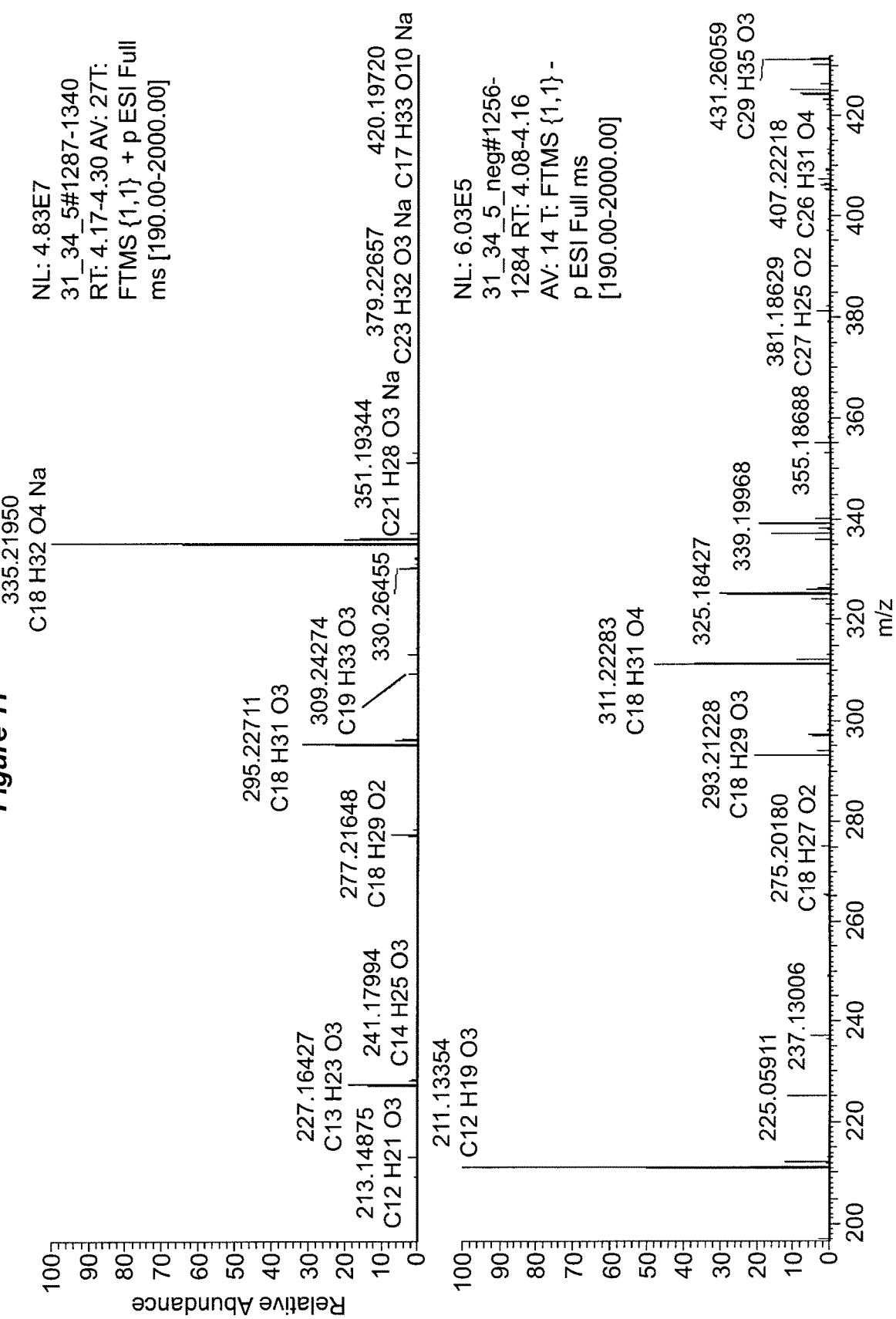
FIG. 11. HRMS spectra of compound of formula (I).
Figure 12:
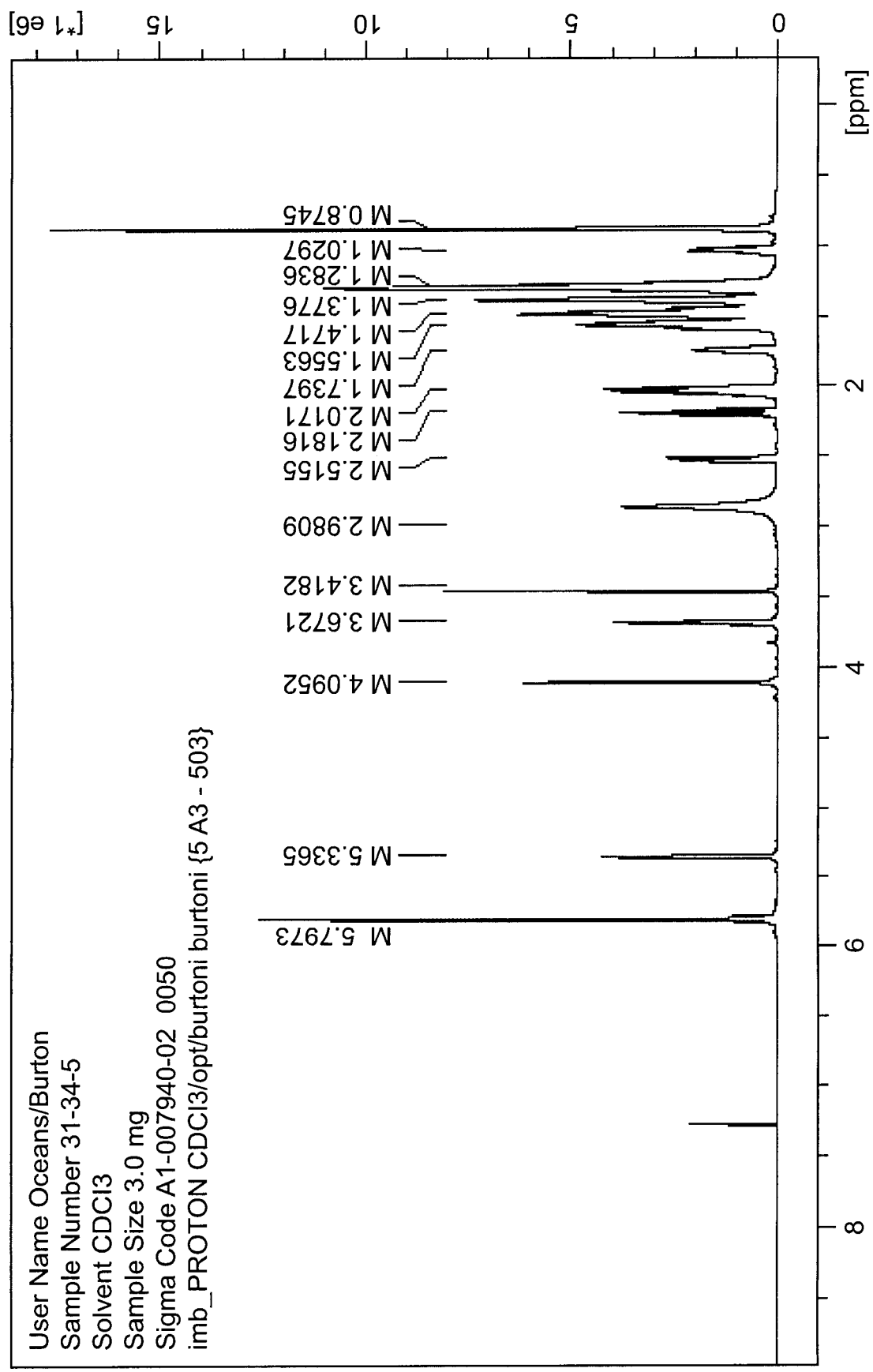
FIG. 12. $^1$H-NMR spectrum of compound of formula (I).
Figure 13:
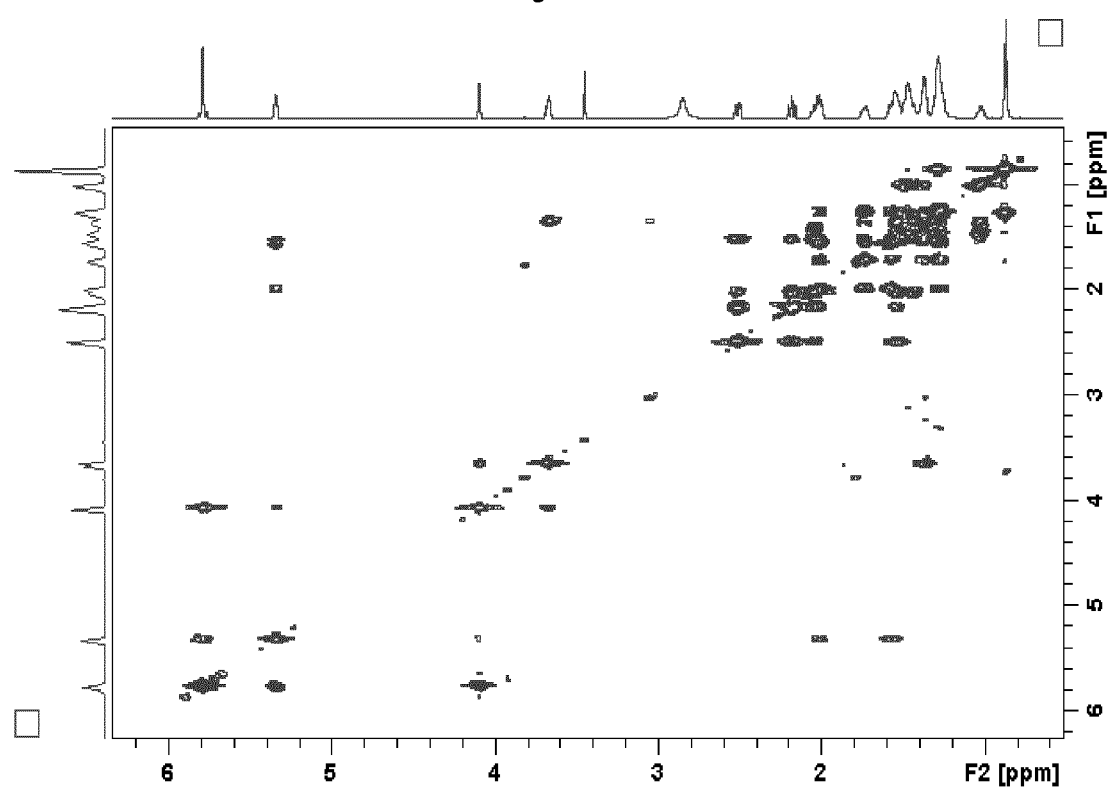
FIG. 13. COSY spectrum of compound of formula (I).
Figure 14:
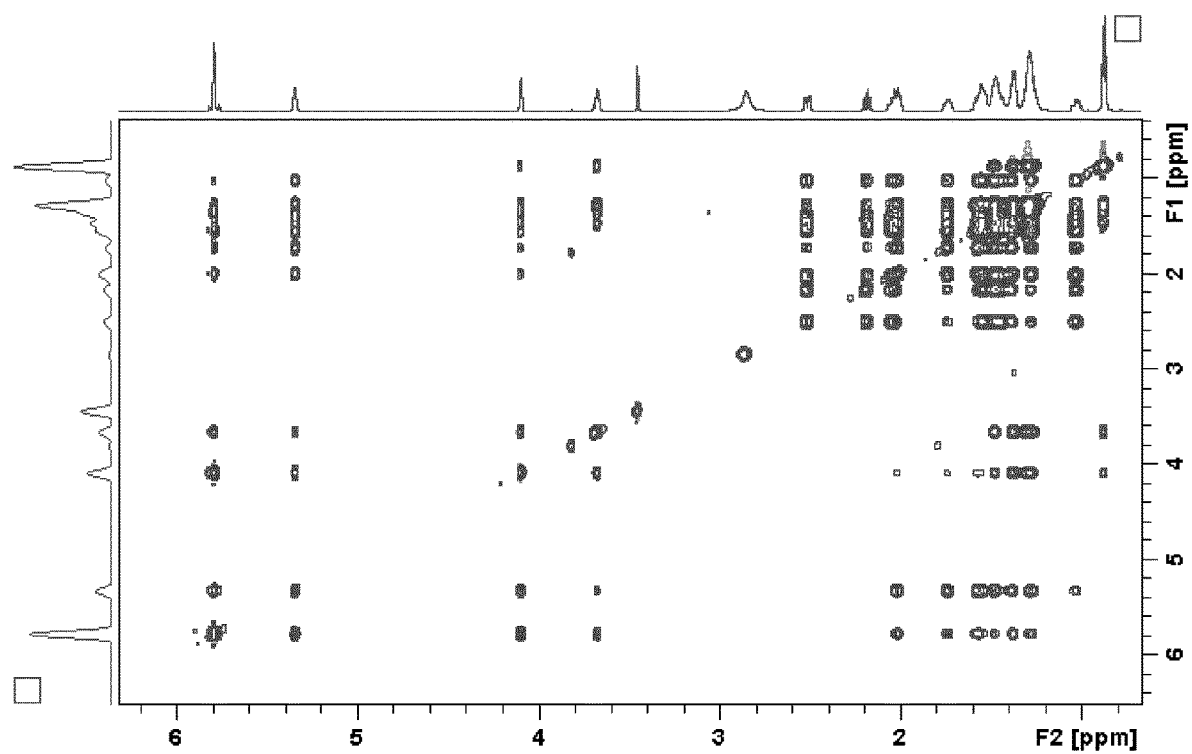
FIG. 14. TOCSY spectrum of compound of formula (I).
Figure 15:
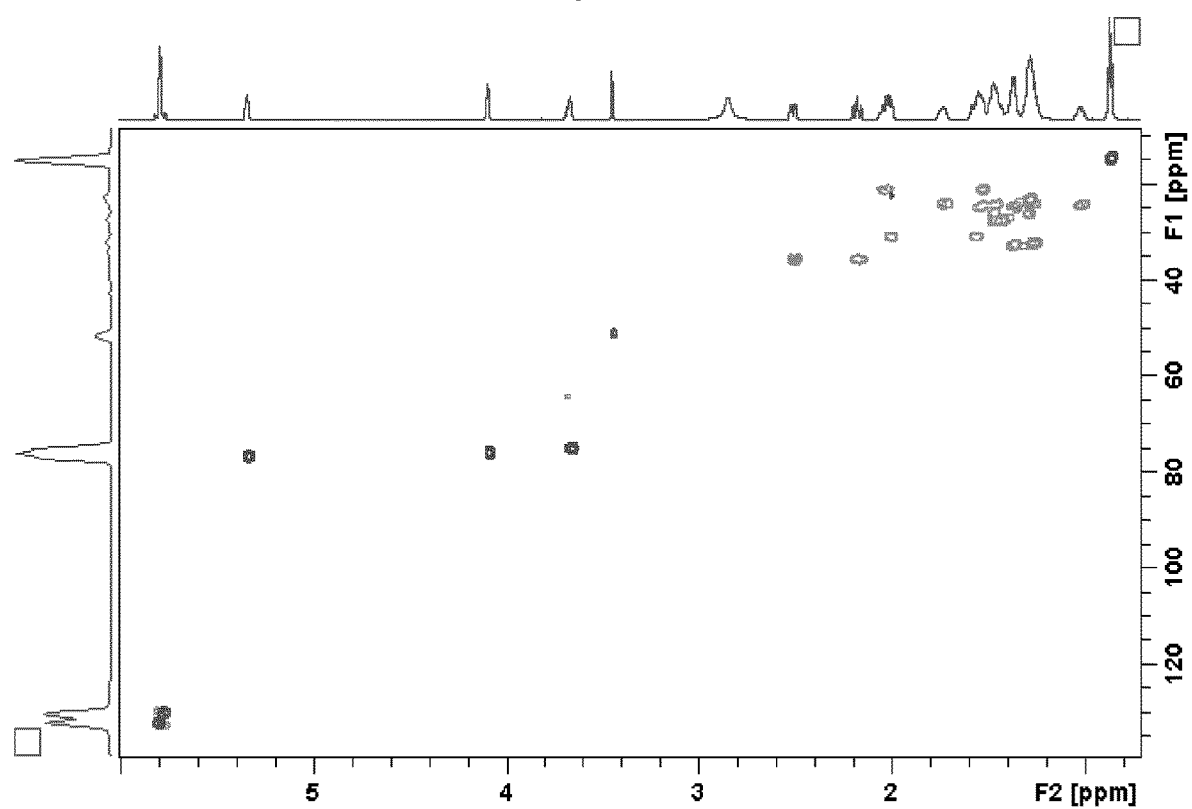
FIG. 15. HSQC spectrum of compound of formula (I).

UPLC-DAD/ELSD/HRMS data (FIG. 10) revealed compound 31-34-5 as a pure compound. HRMS (FIG. 11) peaks of m/z 335.21950 (positive mode, observed for $C_{18}H_{32}O_4Na^+$, calculated 335.21983) and m/z 311.22283 (negative mode, observed for $C_{18}H_{31}O_4^-$, calculated 311.22223) confirmed the molecular formula of $C_{18}H_{32}O_4$.

$^1$H-NMR, COSY, TOCSY, and HSQC spectra (FIGS. 12-15) showed the presence of 2 olefinic methines (δ5.79 ppm), 3 oxygenated methines (δ5.34, 4.09, 3.67 ppm), 11 methylenes (δ2.6-1.0 ppm), and 1 terminal methyl group (δ0.87 ppm).

Figure 16:
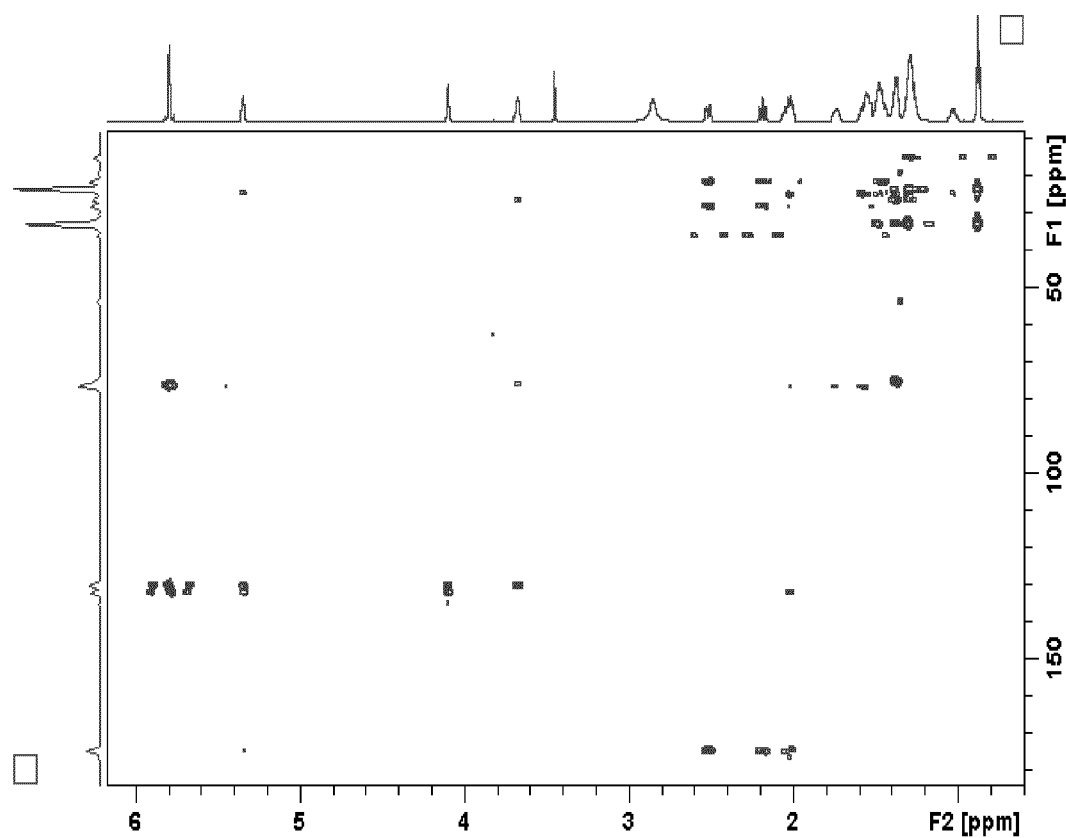
FIG. 16. HMBC spectrum of compound of formula (I).

HMBC (FIG. 16) revealed the key C—H correlations that lead to proposing 12,13-dihydroxy-10-octadecen-9-olide as the structure for compound 31-34-5 (arrows for key HMBC correlations):

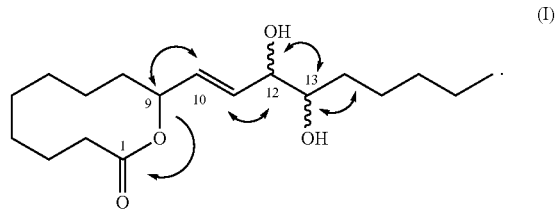 [SMILES: CCCCCC(O)C(O)/C=C/C1CCCCCCCC(=O)O1]

(I)

Figure 17:
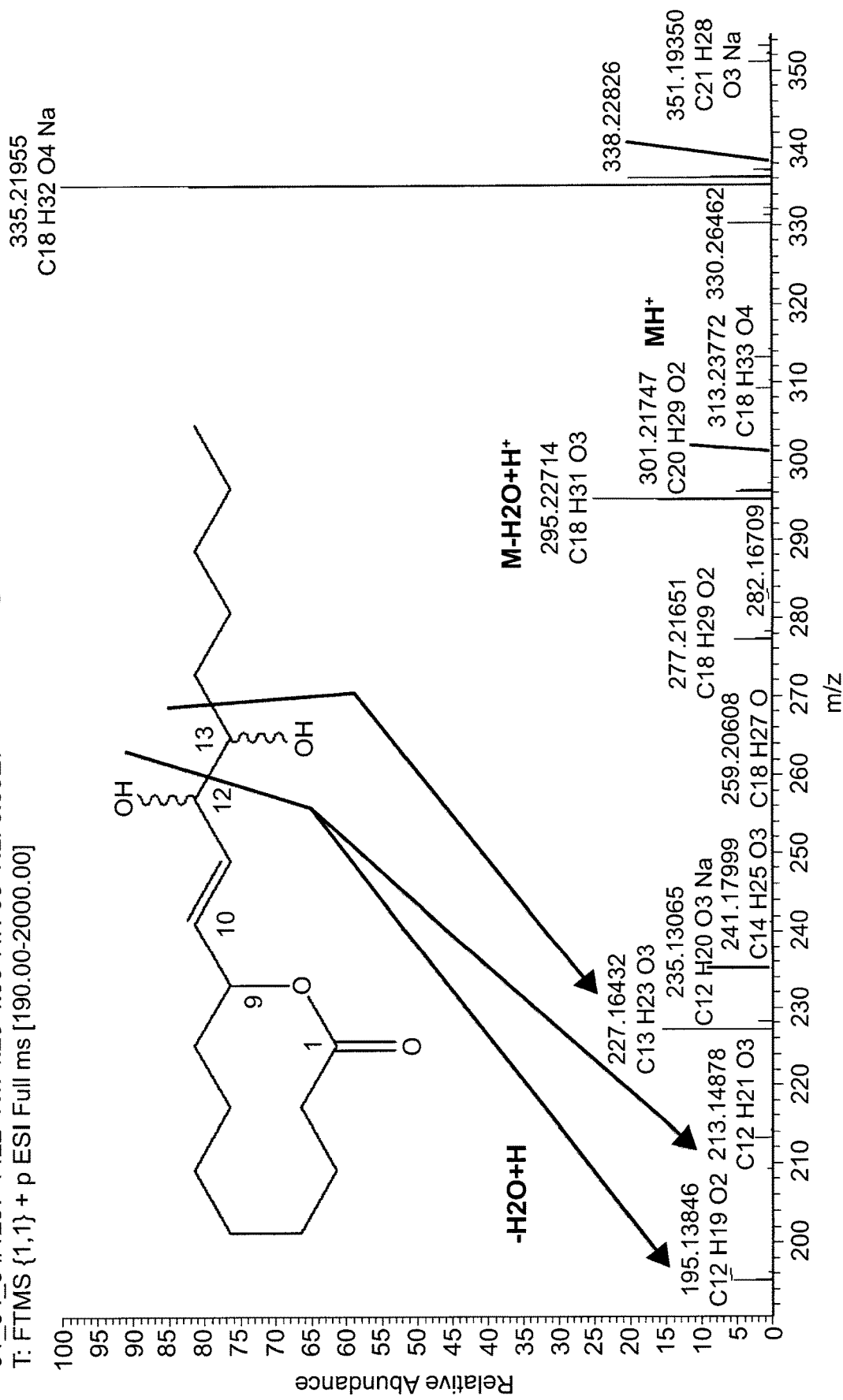
FIG. 17. Fragment ions observed in HRMS for compound of formula (I).

The double bond at C-10, 11 was determined to be trans form based on the coupling J value of the olefinic protons. HRMS (FIG. 17) fragment ions also confirmed the structure.

Based on databases structure search, compound 31-34-5 is a novel compound. It is a fatty acid derivative, likely formed through esterification of unsaturated and oxygenated octadecanoic acid or stearic acid (18:0). Full spectral data assignment is listed in Table 11.

TABLE 11

NMR data of compound 31-34-5

| Position | dC, ppm | type | dH, ppm (J in Hz) |
|---|---|---|---|
| 1 | 175.3 | C=O | |
| 2 | 36.7 | CH$_2$ | 2.51 ddd (15.9; 6.4; 3.3) |
| | | | 2.18 td (13.6; 2.8) |
| 3 | 21.7 | CH$_2$ | 2.04 m |
| | | | 1.54 m |
| 4 | 28.2 | CH$_2$ | 1.45 m |
| 5 | 25.3 | CH$_2$ | 1.54 m |
| | | | 1.36 m |
| 6 | 24.9 | CH$_2$ | 1.45 m |
| | | | 1.02 m |
| 7 | 24.7 | CH$_2$ | 1.70 m |
| | | | 1.23 m |
| 8 | 31.4 | CH$_2$ | 1.97 m |
| | | | 1.55 m |

TABLE 11-continued

NMR data of compound 31-34-5

| Position | dC, ppm | type | dH, ppm (J in Hz) |
|---|---|---|---|
| 9 | 76.7 | CH | 5.34 m |
| 10 | 132.6 | CH | 5.78 dd (15.9; 4.6) |
| 11 | 130.4 | CH | 5.76 dd (15.9; 5.0) |
| 12 | 76.2 | CH | 4.08 br.s |
| 13 | 75.3 | CH | 3.64 br.s |
| 14 | 33.1 | $CH_2$ | 1.37 m |
| 15 | 26.8 | $CH_2$ | 1.47 m |
|   |      |       | 1.29 m |
| 16 | 32.9 | $CH_2$ | 1.29 m |
| 17 | 23.6 | $CH_2$ | 1.29 m |
| 18 | 14.7 | $CH_3$ | 0.87 t (7.1) |

Example 8. In Vitro Anti-Cancer Activity of Compound of Formula (I)

The in vitro anti-cancer activity of compound (I) is presented as average cell viability in Table 12, whereas Table 13 presents the same data but as fold change viability±standard error.

TABLE 12

| Vehicle cont-DMSO | 1% | 96 | 86 | 98 | 93 | 92 | 91 | 88 |
| Positive cont-SDS | 250 ug/ml | 8 | 11 | 4 | 9 | 14 | 5 | 16 |

| Sample # | Sample ID | Ug/mL | PC3 | A549 | U373 | SKOV | MDA-MB | CCD | THP-1 |
|---|---|---|---|---|---|---|---|---|---|
| 3 | 31-34-5 | 100 | 19 | 61 | 3 | 85 | 20 | 17 | 44 |
|   |        | 50  | 97 | 92 | 68 | 94 | 66 | 90 | 68 |
|   |        | 10  | 93 | 93 | 85 | 97 | 96 | 84 | 84 |
|   |        | 1   | 100 | 95 | 90 | 97 | 101 | 91 | 96 |

TABLE 13

|  | PC3 | | A549 | | U373 | | SKOV | |
| ug/mL | AVG | ERROR | AVG | ERROR | AVG | ERROR | AVG | ERROR |
|---|---|---|---|---|---|---|---|---|
| 100 | 0.19 | 0.02 | 0.72 | 0.11 | 0.03 | 0.00 | 0.92 | 0.01 |
| 50 | 1.01 | 0.06 | 1.08 | 0.02 | 0.69 | 0.06 | 1.01 | 0.05 |
| 10 | 0.96 | 0.01 | 1.09 | 0.01 | 0.86 | 0.02 | 1.05 | 0.02 |
| 1 | 1.03 | 0.12 | 1.11 | 0.07 | 0.92 | 0.04 | 1.04 | 0.01 |

|  | MDA-MB | | CCD | | THP-1 | |
| ug/mL | AVG | ERROR | AVG | ERROR | AVG | ERROR |
|---|---|---|---|---|---|---|
| 100 | 0.21 | 0.01 | 0.18 | 0.02 | 0.50 | 0.06 |
| 50 | 0.72 | 0.08 | 0.99 | 0.09 | 0.77 | 0.05 |
| 10 | 1.05 | 0.06 | 0.92 | 0.02 | 0.95 | 0.01 |
| 1 | 1.10 | 0.05 | 1.00 | 0.03 | 1.09 | 0.03 |

(bold = decrease > 25%).

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

All publications and patent applications cited in this specification are herein incorporated by reference as if each individual publication or patent application were specifically and individually indicated to be incorporated by reference.

The invention claimed is:

1. A compound having the formula (I):

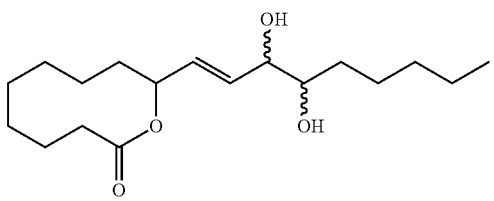

2. The compound of claim 1, as a racemic mixture, or enantiomer thereof.

3. The compound of claim 1, incorporated into a formulation for oral use.

4. The compound of claim 3, wherein said oral formulation is a nutraceutical or nutritional formulation.

5. A seaweed extract enriched in a compound having the formula (I):

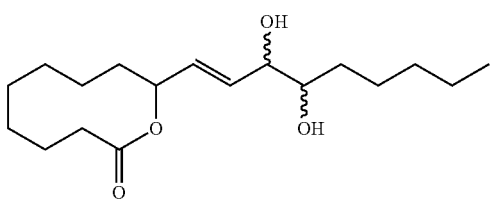

6. A composition comprising the compound of claim 1, in admixture with a physiologically-acceptable excipient.

7. The composition of claim 6, wherein said excipient is orally-acceptable.

8. The oral composition of claim 7, in combination with one or more other therapeutic agent.

9. The composition of claim 8, wherein said other therapeutic agent is an anti-cancer agent.

10. A powder, syrup, gelcap, pill, capsule or other device for oral administration comprising an anti-cancer effective amount of the compound of claim 1.

11. A method for the treatment of cancer in a mammal, comprising administering a growth-inhibiting concentration of the compound of claim 1 to said mammal.

12. The method of claim 11, wherein the mammal is a pet animal or a human.

13. A composition comprising the extract of claim 5, in admixture with a physiologically-acceptable excipient.

14. A method for the treatment of cancer in a mammal, comprising administering a growth-inhibiting concentration of the composition of claim 13 to said mammal.

\* \* \* \* \*